United States Patent
Li et al.

(10) Patent No.: US 12,290,678 B2
(45) Date of Patent: May 6, 2025

(54) IMAGING MARKERS FOR STIMULATOR LEADS

(71) Applicant: Medtronic, Inc., Minneapolis, MN (US)

(72) Inventors: Jiashu Li, Mounds View, MN (US); Patrick Helm, Milton, MA (US); Sean P. Skubitz, Forest Lake, MN (US); Ashutosh Chaturvedi, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 370 days.

(21) Appl. No.: 17/734,277

(22) Filed: May 2, 2022

(65) Prior Publication Data

US 2022/0257929 A1  Aug. 18, 2022

Related U.S. Application Data

(63) Continuation of application No. 16/648,466, filed as application No. PCT/US2018/045995 on Aug. 9, (Continued)

(51) Int. Cl.
*A61N 1/05* (2006.01)
*A61B 90/00* (2016.01)
(Continued)

(52) U.S. Cl.
CPC ............ *A61N 1/0534* (2013.01); *A61B 90/39* (2016.02); *A61N 1/086* (2017.08); *A61N 1/36082* (2013.01); *A61B 2090/3966* (2016.02)

(58) Field of Classification Search
CPC .... A61B 2090/3966; A61B 2090/3995; A61B 6/12; A61B 90/39; A61N 1/05;
(Continued)

(56) References Cited

U.S. PATENT DOCUMENTS 5,203,777 A   4/1993  Lee
6,493,575 B1  12/2002 Kesten et al.
(Continued)

FOREIGN PATENT DOCUMENTS

EP   1602393   12/2005
EP   1661600   5/2006
(Continued)

OTHER PUBLICATIONS

Sapiens Steering Brain Stimulation BV, "How to find out the azimuthal orientation of a stimulation lead?" Prior Art Journal, 2014; 07:93-99.

*Primary Examiner* — George Manuel
(74) *Attorney, Agent, or Firm* — Mueting Raasch Group

(57) ABSTRACT

A sleeve for a medical lead includes a tubular body having a first open end and a second open end, a tubular wall extending between the first and second ends and defining a hollow center, and a longitudinal axis extending through the hollow center. A first pocket is disposed in the tubular wall and having a curved transverse cross section and a first access opening at the first open end of the tubular body. A medical lead system includes a medical lead and the sleeve configured to slide over the medical lead and be adjacent to the electrode region.

18 Claims, 19 Drawing Sheets

Related U.S. Application Data 2018, now Pat. No. 11,318,297, which is a continuation of application No. 15/711,462, filed on Sep. 21, 2017, now abandoned.

(51) Int. Cl.
*A61N 1/08* (2006.01)
*A61N 1/36* (2006.01)

(58) Field of Classification Search
CPC ........ A61N 1/0534; A61N 1/08; A61N 1/086; A61N 1/36082; A61N 1/37514
See application file for complete search history.

(56) References Cited

U.S. PATENT DOCUMENTS

| | | | |
|---|---|---|---|
| 7,706,889 B2 | 4/2010 | Gerber et al. | |
| 7,765,012 B2 | 7/2010 | Gerber | |
| 7,774,072 B2 | 8/2010 | Gerber | |
| 7,879,024 B2 | 2/2011 | Thorstenson et al. | |
| 7,996,091 B2 | 8/2011 | Harris | |
| 8,224,456 B2 | 7/2012 | Daglow et al. | |
| 8,326,433 B2 | 12/2012 | Blum et al. | |
| 8,449,527 B2 | 5/2013 | Thorstenson et al. | |
| 8,452,415 B2 | 5/2013 | Goetz et al. | |
| 8,463,401 B2 | 6/2013 | Jones et al. | |
| 8,571,685 B2 | 10/2013 | Daglow et al. | |
| 8,620,452 B2 | 12/2013 | King et al. | |
| 8,674,945 B2 | 3/2014 | Seo | |
| 8,744,596 B2 | 6/2014 | Howard | |
| 8,831,731 B2 | 9/2014 | Blum et al. | |
| 8,831,742 B2 | 9/2014 | Pianca et al. | |
| 8,849,632 B2 | 9/2014 | Sparks et al. | |
| 8,855,773 B2 | 10/2014 | Kokones et al. | |
| 8,855,882 B2 | 10/2014 | Yoshii | |
| 8,923,982 B2 | 12/2014 | Howard | |
| 9,026,217 B2 | 5/2015 | Kokones et al. | |
| 9,050,470 B2 | 6/2015 | Carlton et al. | |
| 9,063,643 B2 | 6/2015 | Sparks et al. | |
| 9,072,905 B2 | 7/2015 | Kokones et al. | |
| 9,084,881 B2 | 7/2015 | Sage et al. | |
| 9,084,896 B2 | 7/2015 | Kokones et al. | |
| 9,162,056 B2 | 10/2015 | Pianca | |
| 9,220,889 B2 | 12/2015 | Carlton et al. | |
| 9,254,387 B2 | 2/2016 | Blum et al. | |
| 9,259,589 B2 | 2/2016 | Goetz et al. | |
| 9,272,153 B2 | 3/2016 | Blum et al. | |
| 9,302,110 B2 | 4/2016 | Kokones et al. | |
| 9,308,372 B2 | 4/2016 | Sparks et al. | |
| 9,310,985 B2 | 4/2016 | Blum et al. | |
| 9,370,653 B2 | 6/2016 | Sefkow et al. | |
| D766,601 S | 9/2016 | Barre et al. | |
| 9,492,657 B2 | 11/2016 | Gerber | |
| 9,501,829 B2 | 11/2016 | Carlton et al. | |
| 9,526,902 B2 | 12/2016 | Blum et al. | |
| 9,675,795 B2 | 6/2017 | Pianca et al. | |
| 2005/0059990 A1* | 3/2005 | Ayala | A61M 25/0662 606/192 |
| 2006/0142656 A1* | 6/2006 | Malackowski | A61F 2/4609 600/424 |
| 2006/0247748 A1 | 11/2006 | Wahlstrand et al. | |
| 2008/0103572 A1 | 5/2008 | Gerber | |
| 2008/0103576 A1 | 5/2008 | Gerber | |
| 2008/0132979 A1 | 6/2008 | Gerber | |
| 2009/0112084 A1 | 4/2009 | Piferi et al. | |
| 2009/0177077 A1 | 7/2009 | Piferi et al. | |
| 2009/0306728 A1 | 12/2009 | Wright et al. | |
| 2011/0196410 A1* | 8/2011 | Besselink | A61M 29/02 606/191 |
| 2012/0016378 A1 | 1/2012 | Pianca et al. | |
| 2012/0265267 A1 | 10/2012 | Blum et al. | |
| 2012/0277621 A1 | 11/2012 | Gerber et al. | |
| 2012/0277670 A1 | 11/2012 | Goetz et al. | |
| 2013/0131768 A1 | 5/2013 | Possover | |
| 2013/0317587 A1 | 11/2013 | Barker | |
| 2014/0039590 A1 | 2/2014 | Moffitt et al. | |
| 2014/0180068 A1 | 6/2014 | Spencer et al. | |
| 2014/0243821 A1 | 8/2014 | Salahieh et al. | |
| 2014/0257444 A1 | 9/2014 | Cole et al. | |
| 2014/0350694 A1 | 11/2014 | Behan | |
| 2015/0011871 A1 | 1/2015 | Bradley et al. | |
| 2015/0080995 A1 | 3/2015 | Seeley et al. | |
| 2015/0142090 A1 | 5/2015 | Duijsens et al. | |
| 2015/0157851 A1 | 6/2015 | Sefkow et al. | |
| 2015/0245848 A1 | 9/2015 | Shimon | |
| 2015/0283389 A1 | 10/2015 | Stone et al. | |
| 2015/0297893 A1 | 10/2015 | Kokones et al. | |
| 2016/0048962 A1 | 2/2016 | Carlton et al. | |
| 2016/0059004 A1 | 3/2016 | Mercanzini et al. | |
| 2016/0121103 A1 | 5/2016 | Villarta et al. | |
| 2016/0206380 A1 | 7/2016 | Sparks et al. | |
| 2016/0263370 A1 | 9/2016 | Sefkow et al. | |
| 2016/0375257 A1 | 12/2016 | Goetz et al. | |
| 2017/0021451 A1 | 1/2017 | Drexler et al. | |
| 2017/0043156 A1 | 2/2017 | Possover | |
| 2017/0056678 A1 | 3/2017 | Bokil | |
| 2017/0061627 A1 | 3/2017 | Bokil | |
| 2020/0230397 A1 | 7/2020 | Li et al. | |

FOREIGN PATENT DOCUMENTS

| | | |
|---|---|---|
| EP | 2522389 | 8/2014 |
| EP | 2321004 | 6/2016 |
| JP | 2015500705 A | 1/2015 |
| JP | 2015181773 A | 10/2015 |
| WO | 2005/067792 | 7/2005 |
| WO | 2007/123443 A1 | 11/2007 |
| WO | 2008/038208 | 4/2008 |
| WO | 2008/133616 A1 | 11/2008 |
| WO | 2015/143327 | 9/2015 |

\* cited by examiner

IMAGING MARKERS FOR STIMULATOR LEADS

FIELD

The present disclosure relates to implantable medical leads used for electrical stimulation. In particular, the present disclosure relates to imaging markers for such implantable medical leads.

BACKGROUND

Various medical conditions can be treated using neurological stimulation. Such conditions include, for example, pain, movement disorders, epilepsy, depression, pelvic floor disorders, gastroparesis, and a wide variety of other medical conditions. Neurostimulation systems may include an implantable neurostimulator with an electrical stimulator lead. Stimulator leads typically include a plurality of electrodes, which may be implanted within or proximate to a specific location in the patient to deliver stimulation to structures or tissues at a target location in the patient. Some therapies involve electrical stimulation of the brain, spinal cord, or pelvic floor. Still other therapies involve electrical stimulation of other sites in the patient.

One example of electrical stimulation therapy is deep brain stimulation (DBS), which involves delivery of electrical stimulation to nerve structures in specific areas of the brain to either excite or inhibit cell activity. DBS can be effective in the management of, for example chronic pain, movement disorders such as Parkinson's disease and essential tremor, epilepsy, and psychiatric disorders such as depression and obsessive-compulsive disorder. A stimulator lead is typically implanted at a desired location within the brain with relative precision using various imaging techniques, such as magnetic resonance imaging (MM), computerized tomography (CT), X-ray, fluoroscopic imaging, and stereotactic imaging.

Stimulator leads with segmented rows of electrodes, in which each of the electrodes does not extend around the full periphery, e.g., circumference, of the lead body, may be desired for targeted stimulation or for efficient use of energy. With respect to targeted stimulation, electrodes in segmented rows may, for example, generate stimulation fields that are skewed in a particular radial direction from the lead, as opposed to the fields produced by ring electrodes, which are substantially equal in all radial directions when stimulating within homogeneous tissue. The ability to direct the stimulation field in this manner may permit particular stimulation targets to be activated, while avoiding other areas. This ability may be advantageous in the case of DBS, as well as other types of stimulation.

When treating a patient with electrical stimulation therapy, a physician selects values for a number of programmable parameters in order to define the stimulation to be delivered by the implantable stimulator lead to the patient. For example, the physician may select a combination of electrodes carried by the implantable lead, and assigns polarities to the selected electrodes. In addition, the physician selects an amplitude, which may be a current or voltage amplitude, a pulse width, and a pulse rate for stimulation pulses to be delivered to the patient. A group of parameters, including electrode combination, electrode polarity, amplitude, pulse width and pulse rate, may be referred to as a program in the sense that they drive the neurostimulation therapy to be delivered to the patient. In selecting the parameters, the physician may need to balance clinical efficacy with minimal side effects experienced by the patient.

Precise placement and orientation of the stimulator lead within the patient (e.g., the patient's brain) is desired for delivery of the electrical stimulation to the intended location and for avoiding side effects. In some applications, it is desirable to position the stimulator lead to deliver stimulation to a very small target site without stimulating adjacent brain tissue. If stimulation is not delivered with precision to a desired target site, adjoining areas may also be stimulated, which may lead to reduced efficacy. Improvements to the ability precisely place and orient the stimulator lead are desired.

SUMMARY

The present disclosure relates to implantable medical leads used for electrical stimulation. In particular, the present disclosure relates to imaging markers for such implantable medical leads.

According to an aspect, a medical lead includes a main body having a length extending from a proximal end to a distal end, a longitudinal axis parallel to the length, and a proximal portion adjacent to the proximal end and a distal portion adjacent to the distal end; a plurality of electrodes defining an electrode region positioned on the main body in the distal portion; and an imaging marker positioned between the electrode region and the proximal end and separated from the electrode region by a distance in an axial direction, the imaging marker comprising a first marker segment and a second marker segment. The first marker segment defines a first center point and a first marker surface occupying a first arc on the main body, and the second marker segment defines a second center point and a second marker surface occupying a second arc on the main body separated from the first arc by an intermediate arc. The second center point is radially separated from the first center point by about 100 to about 145 degrees. The intermediate arc may have an angle up to about 60 degrees. The distance between the imaging marker and the electrode region may be 3 mm or greater.

According to another aspect, a medical lead includes a main body having a length extending from a proximal end to a distal end, a longitudinal axis parallel to the length, and a proximal portion adjacent to the proximal end and a distal portion adjacent to the distal end; a plurality of electrodes defining an electrode region positioned on the main body in the distal portion; and an imaging marker positioned between the electrode region and the proximal end and separated from the electrode region by at least 3 mm in an axial direction. The imaging marker at least partially surrounds the main body, occupying an arc of about 50 to about 90 degrees on the main body, the arc being perpendicular to the longitudinal axis of the main body.

According to another aspect, the medical lead is operatively connected to an implantable medical device.

According to an aspect, the imaging marker is covered by an electrically insulating layer.

In one aspect, the imaging marker is disposed in a sleeve. The sleeve includes a tubular body having a first open end and a second open end, a tubular wall extending between the first and second ends and defining a hollow center, and a longitudinal axis extending through the hollow center; and a first pocket disposed in the tubular wall and having a curved transverse cross section and a first access opening at the first open end of the tubular body. The first pocket may be sized to receive an imaging marker. The sleeve may also include a second pocket sized to receive a second imaging marker. The first and second pockets may each have a longitudinal center line, the longitudinal center lines being separated by about 100 to about 140 degrees about the longitudinal axis of the tubular body.

DETAILED DESCRIPTION

Figure 1:
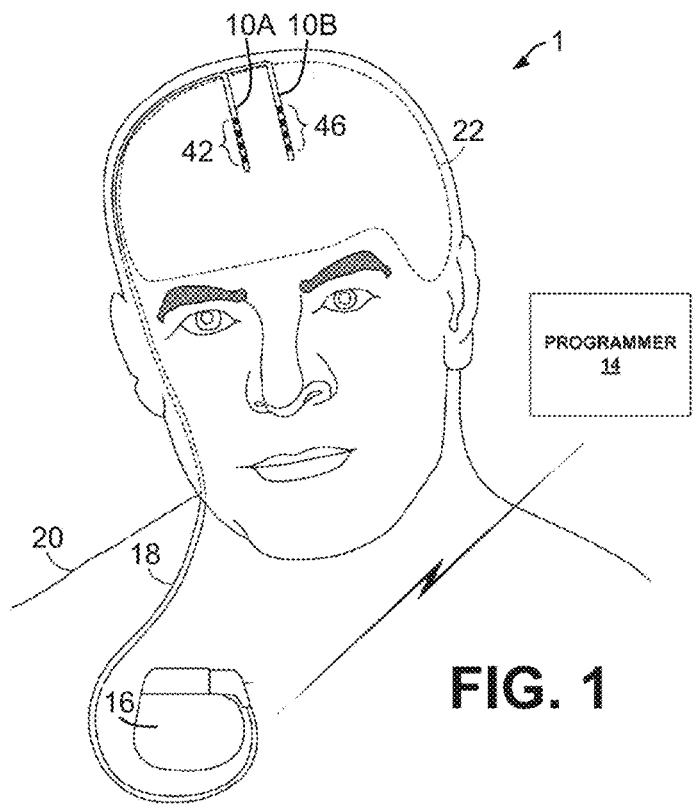
FIG. 1 is schematic diagram illustrating the use of an example deep brain stimulation (DBS) system of this disclosure.

The present disclosure relates to implantable medical leads used for electrical stimulation that include an imaging marker for aiding with the placement and orientation of the medical leads.

Reference numbers are used in the Figures and the accompanying description to refer to elements of the described device. The same or similar reference numbers (e.g., 10 and 10') are used to refer to the same element throughout the description and Figures.

The term "about" is used here in conjunction with numeric values to include normal variations in measurements as expected by persons skilled in the art, and is understood have the same meaning as "approximately" and to cover a typical margin of error, such as ±5% of the stated value.

Terms such as "a," "an," and "the" are not intended to refer to only a singular entity, but include the general class of which a specific example may be used for illustration.

Stimulator leads for deep brain stimulation may include stimulation electrodes. Deep brain stimulation devices and leads have been described in the art, including in U.S. Pat. No. 7,668,601 (Hegland et al.), which described stimulator leads that include segmented electrodes for improved precision of the electric stimulation signals.

Implantable electrical stimulators incorporating one or more leads with complex electrode array geometries may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. For example, stimulation may be delivered via complex electrode array geometries to serve different therapeutic applications, such as deep brain stimulation (DBS), spinal cord stimulation (SCS), pelvic stimulation, gastric stimulation, or peripheral nerve stimulation. Stimulation via complex electrode array geometries may also be used for muscle stimulation, e.g., functional electrical stimulation (FES) to promote muscle movement or prevent atrophy. In addition, stimulation may be delivered via one, two, or more leads. The stimulator leads will be described as used in DBS for purposes of illustration throughout this disclosure, but this use should not be considered limiting of the present disclosure.

DBS may be used to treat dysfunctional neuronal activity in the brain which manifests as diseases or disorders such as Huntington's Disease, Parkinson's Disease, or movement disorders, for example. The exact mechanisms explaining why electrical stimulation therapy is capable of treating such conditions of the brain are not fully known, but symptoms of these diseases can be lessened or eliminated with stimulation therapy. Certain anatomical regions of brain are responsible for producing the symptoms of brain disorders. For example, stimulating an anatomical region called the substantia nigra in the brain may reduce the number and magnitude of tremors experienced by the patient. Other examples include stimulation of the subthalamic nucleus, globus pallidus interna, ventral intermediate nucleus, or zona inserta. During implantation of the stimulator lead, the physician attempts to position the lead as close to the desired region as possible.

Although DBS may successfully reduce symptoms of some neurological diseases, the stimulation commonly causes unwanted side effects, as well. Side effects may include incontinence, tingling, loss of balance, paralysis, slurred speech, loss of memory, and many other neurological problems. While side effects may be mild to severe, most side effects are reversible when stimulation is stopped. DBS may cause one or more side effects by inadvertently providing electrical stimulation pulses to anatomical regions near the targeted anatomical region.

In some applications, it is desirable to position the stimulator lead to deliver stimulation to a very small target site without stimulating adjacent brain tissue. In sensitive areas of the body, such as in the brain, orienting the lead correctly can be particularly important yet difficult. The cross dimensions of the lead are typically very small and the orientation of the lead may be judged using imaging techniques, such as CT scanning, that may have a resolution that is only slightly smaller than the cross dimension of the lead.

The present disclosure provides improved orientation markers for directional leads that may provide stimulation in a non-uniform manner in one or more selected directions around the circumference of the lead. These orientation markers can be detected using commonly used imaging methods either during placement of an implanted lead or after the implant has been placed. Exemplary imaging methods include magnetic resonance imaging (MRI), computerized tomography (CT), X-ray, fluoroscopic imaging, and stereotactic imaging (e.g., by O-ARM® available from Medtronic, Inc. in Dublin, Ireland). Easier orientation of the lead can reduce the time physicians need to identify the electrode's orientation with respect to the relevant brain structure or other body part. The stimulator leads of the present disclosure can also reduce side effects of stimulation therapy while maximizing therapeutic benefits.

Figure 13:
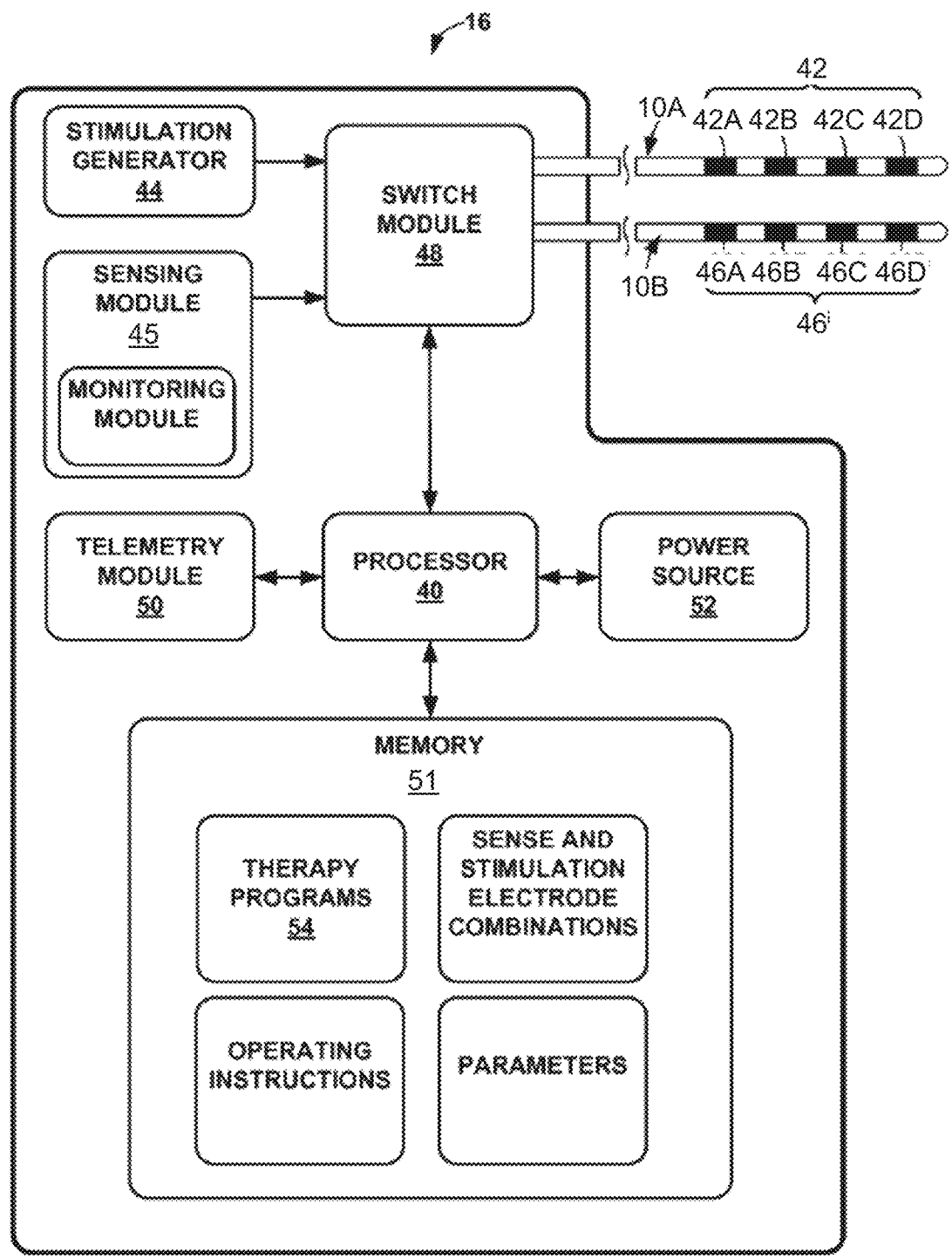
FIG. 13 is functional block diagram illustrating components of an example medical device that may be used to in connection with the stimulator lead of FIG. 2.

FIG. 1 shows an example environment of a stimulator lead 10 in use according to an embodiment. In the example shown, the therapy system 1 includes medical device programmer 14, implantable medical device (IMD) 16, lead extension 18, and leads 10A and 10B with respective sets of electrodes 42, 46 (FIG. 13 illustrates electrodes 42A, 42B, 42C, 42D, and 46A, 46B, 46C, 46D). In the example shown in FIG. 1, electrodes 42, 46 of leads 10A, 10B are positioned to deliver electrical stimulation to a tissue site within brain 22, such as a deep brain site under the dura mater of brain 22 of patient 20. In some examples, delivery of stimulation to one or more regions of brain 22, such as the subthalamic nucleus, globus pallidus internus or thalamus, may be an effective treatment to manage movement disorders, such as Parkinson's disease or essential tremor.

IMD 16 may include a therapy module that includes a stimulation generator that generates and delivers electrical stimulation therapy to patient 20 via a subset of electrodes 42, 46 of leads 10A and 10B, respectively. The subset of electrodes 42, 46 that are used to deliver electrical stimulation to patient 20, and, in some cases, the polarity of the subset of electrodes 42, 46, may be referred to as a stimulation electrode combination.

The stimulator lead 10 includes a main body 100 with a proximal end 101 (see, for example, FIG. 2) connected to the IMD 16, and a distal end 102 intended to be implanted into the patient. When the stimulator is used to stimulate an area of the brain, the distal end 102 of the stimulator lead 10 can be inserted through a hole in the cranium, e.g., via a burr hole cap. In some cases, more than one stimulator lead 10 may be implanted to stimulate multiple regions. For example, in some therapies, leads may be positioned in two hemispheres of the brain as shown in FIG. 1.

FIG. 13 is a functional block diagram illustrating components of an example IMD 16. In the example shown in FIG. 13, IMD 16 includes processor 40, memory 51, stimulation generator 44, sensing module 45, switch module 48, telemetry module 50, and power source 52. Memory 51 may include any volatile or non-volatile media, such as a random-access memory (RAM), read only memory (ROM), non-volatile RAM (NVRAM), electrically erasable programmable ROM (EEPROM), flash memory, and the like. Memory 51 may store computer-readable instructions that, when executed by processor 40, cause IMD 16 to perform various functions.

In the example shown in FIG. 13, memory 51 stores therapy programs 54 to control delivery of stimulation therapy to the patient. Each stored therapy program 54 may define a particular program of therapy in terms of respective values for electrical stimulation parameters, such as a stimulation electrode combination, electrode polarity, current or voltage amplitude, pulse width, and pulse rate. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Stimulation generator 44 may generate and deliver electrical stimulation therapy to the patient according to the set of stored programs or stimulation parameters. Stimulation generator 44 may be a single channel or multi-channel stimulation generator. In particular, stimulation generator 44 may be capable of delivering a single stimulation pulse, multiple stimulation pulses or continuous signal at a given time via a single electrode combination, or multiple stimulation pulses or continuous signals at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

As discussed above, in some examples, IMD may include a sensing module 45, which under the control of processor 40, may sense bioelectrical brain signals and provide the sensed bioelectrical brain signals to processor 40. Processor 40 may control switch module 48 to couple sensing module 45 to selected combinations of electrodes 42, 46 through which IMD may sense bioelectrical brain signals. Sensed bioelectrical brain signals may be used for diagnosis, determine a state of a patient, determine disease progression, and/or be used to control closed-loop therapy (e.g., to deliver closed-loop stimulation).

Telemetry module 50 supports wireless communication between IMD 16 and an external programmer 14 (see FIG. 1) or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

As depicted in the figures, DBS leads may include one or more ring electrodes placed along the longitudinal axis of the stimulator lead. Each ring electrode extends around the entire circumference of the lead. Therefore, electrical current from the ring electrodes propagates radially in all directions from the electrode when activated. The resulting stimulation field reaches anatomical regions of brain within a certain distance in all directions. The stimulation field may reach the target anatomical region, but may also affect non-target anatomical regions and produce unwanted side effects. Implanting a lead with a more complex electrode array geometry may help customize the stimulation field and provide improved therapy while decreasing side effects. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead, in addition to, or instead of, a ring electrode. In this manner, electrical stimulation may be directed to a specific direction from leads to enhance therapy efficacy and reduce possible adverse side effects from stimulating a large volume of tissue. As a further example, the electrodes may be pad electrodes, which may be carried on a paddle lead or a cylindrical lead. Using this type of complex electrode array geometry, stimulation fields may be delivered on a more directional basis to more selectively target specific anatomical structures. By selecting electrodes at particular angular positions, a field may be generally limited to one side of a lead rather than all sides of the lead, making the field more directional. In order to be able to position the field in the right direction, the physician needs to be able to detect the orientation of the lead.

Figure 2:
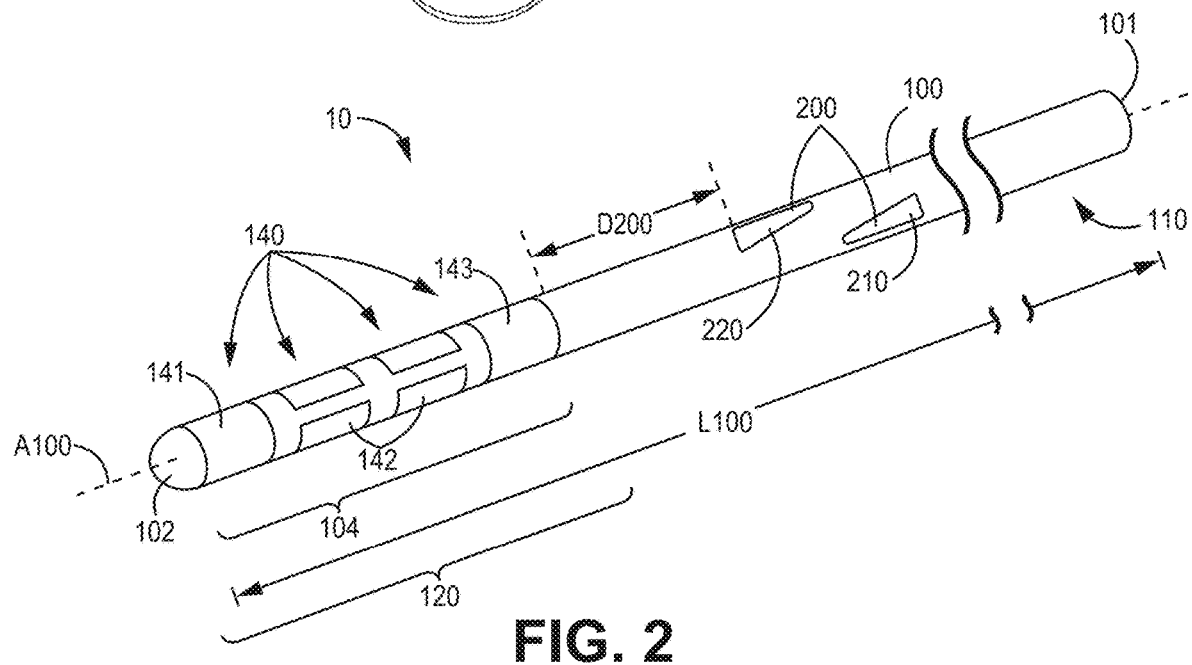
FIG. 2 is a perspective view of a stimulator lead according to an embodiment.

An exemplary stimulator lead 10 with a complex electrode array geometry is shown in FIG. 2. The stimulator lead 10 includes a main body 100 having a length L100 extending from the proximal end 101 to the distal end 102. A longitudinal axis A100 extends through the stimulator lead 10 main body 100 parallel to the length L100. The main body 100 includes a proximal portion 110 adjacent to the proximal end 101, and a distal portion 120 adjacent to the distal end 102. The stimulator lead 10 includes a plurality of electrodes defining an electrode region 104 positioned on the main body 100 in the distal portion 120.

The stimulator lead 10 may also include additional electrodes either in the same electrode region or in an additional electrode region that may be disposed along the main body 100 of the stimulator lead 10. In this disclosure, references to the electrodes and the electrode region refer to the electrode region 104 in the distal portion 120.

In the example of FIG. 2, the stimulator lead 10 includes four electrode "levels" at different axial positions along the length of the lead. Each level includes an electrode generally arranged in a ring, with some of the rings made up of multiple non-contiguous electrode segments. These electrodes may be referred to as segmented electrodes. Each electrode is coupled to a respective electrical conductor within the stimulator lead 10. Hence, the stimulator lead 10 includes multiple electrical conductors, e.g., wires, cables or the like, that extend from the proximal end 101 of the lead 10 to respective electrodes to electrically couple the electrodes to electrical terminals of an associated stimulation current generator.

Although the segments are shown arranged in rows that occupy a cross-section in the example of FIG. 1, this need not be the case. For example, some or all of the electrode segments may occupy a different longitudinal position along the lead body than any other electrode segments. As one specific example, electrode segments may be arranged in a helical pattern around the longitudinal axis of the lead body. Alternatively, the segments may be in "slanted" or "diagonal" rings that don't complete occupy a same cross-section of the lead body. FIG. 2 shows a so-called 1-3-3-1 configuration wherein a first (distal-most) ring electrode 141 is adjacent to two rows of segmented (three-part) electrodes 142, which in turn are adjacent to a second ring electrode 143. In other examples, more or fewer rings may be provided and the rings may be arranged in a different order, such as a 3-3-1-1 lead. In another configuration, the lead may not include ring electrodes, or may not include segmented electrodes. Thus, it will be understood the electrodes may be arranged in many ways on the lead 10, and FIG. 2 is one illustrative example.

The segmented electrodes are positioned at different angular positions around the circumference of the stimulator lead 10, which has a generally circular cross-section in the example of FIG. 2. Each electrode is independently selectable so that stimulation energy can be delivered from the lead at different axial and angular positions. Selective activation of the electrodes carried by the stimulator lead 10 can produce customizable stimulation fields that may be directed to a particular side of the stimulator lead 10 in order to isolate the stimulation field around a target anatomical region of the brain. Producing directional or irregular stimulation fields with the stimulator lead 10 not only allows the electrical stimulation system 1 to more effectively treat certain anatomical regions of the brain, but can also reduce or eliminate side effects relative to spherical stimulation fields produced by leads with simple electrode array geometries.

According to an embodiment, the stimulator lead 10 includes an imaging marker 200 positioned between the electrode region 104 and the proximal end 101. The imaging marker 200 may be made of any suitable material that allows it to be seen in an imaging scan, such as a MRI, CT, X-ray, fluoroscope, or OARM® scan. The imaging marker 200 may be constructed of a material that is suitable for multiple modes of imaging. For example, the imaging marker 200 may be constructed of or include materials that are radio opaque. Examples of suitable materials include metals, such as platinum, iridium, tantalum, and the like, and mixtures thereof. For example, the material may include from about 75% to 100% platinum, or from about 80 to about 90% platinum; from about 5% to about 20% iridium or about 10% iridium; and/or from about 5% to about 20% tantalum or about 10% tantalum. In one embodiment, the imaging marker is made of about 90% platinum and about 10% iridium.

In some embodiments, the imaging marker 200 is disposed along a cylindrical surface that is coaxial with the longitudinal axis A100 of the main body 100. The imaging marker 200 may have a curved shape that follows the contour of the cylindrical surface. However, the cylindrical surface may be further covered by one or more layers of material. In other words, the cylindrical surface is not necessarily the outer surface of the main body 100.

The imaging marker 200 is preferably positioned and configured such that the angular orientation of the stimulator lead 10 can be detected from an imaging scan, including MRI, CT, X-ray, fluoroscope, and O-OARM® scans. Certain imaging techniques, such as certain 3D scanning techniques, impose some limitations on the imaging marker due to their resolution. For example, CT scans are commonly performed at a resolution of 1 mm×1 mm×1 mm, and imaging markers with dimensions smaller than 1 mm may thus be missed in a CT scan. CT scans may also cause a scattering artifact causing some blurring of the image. It has been found that certain imaging marker configurations can alleviate this effect.

The imaging marker 200 may be separated from the electrode region 104 by a distance D200 in an axial direction. In some cases where the imaging marker 200 is made of a conducting material, the imaging marker 200 may be activated by a near-by electrode (e.g., the proximal-most electrode in the electrode region 104) thus resulting in unwanted tissue activation around the imaging marker. The distance D200 between the imaging marker 200 and the electrode region 104 may be selected to be sufficient to avoid activation of the imaging marker 200. In some embodiments, the imaging marker 200 is separated from the electrode region 104 by a distance D200 of at least 3.0 mm, at least 3.5 mm, at least 4.0 mm, at least 4.5 mm, at least 5.0 mm, at least 5.5 mm, or at least 6.0 mm. The distance D200 may be up to 20 mm, up to 15 mm, or up to 10 mm. The imaging marker 200 may additionally be insulated by providing a layer of electrically non-conducting material (e.g., a polymer) to cover the imaging marker 200.

Figure 5:
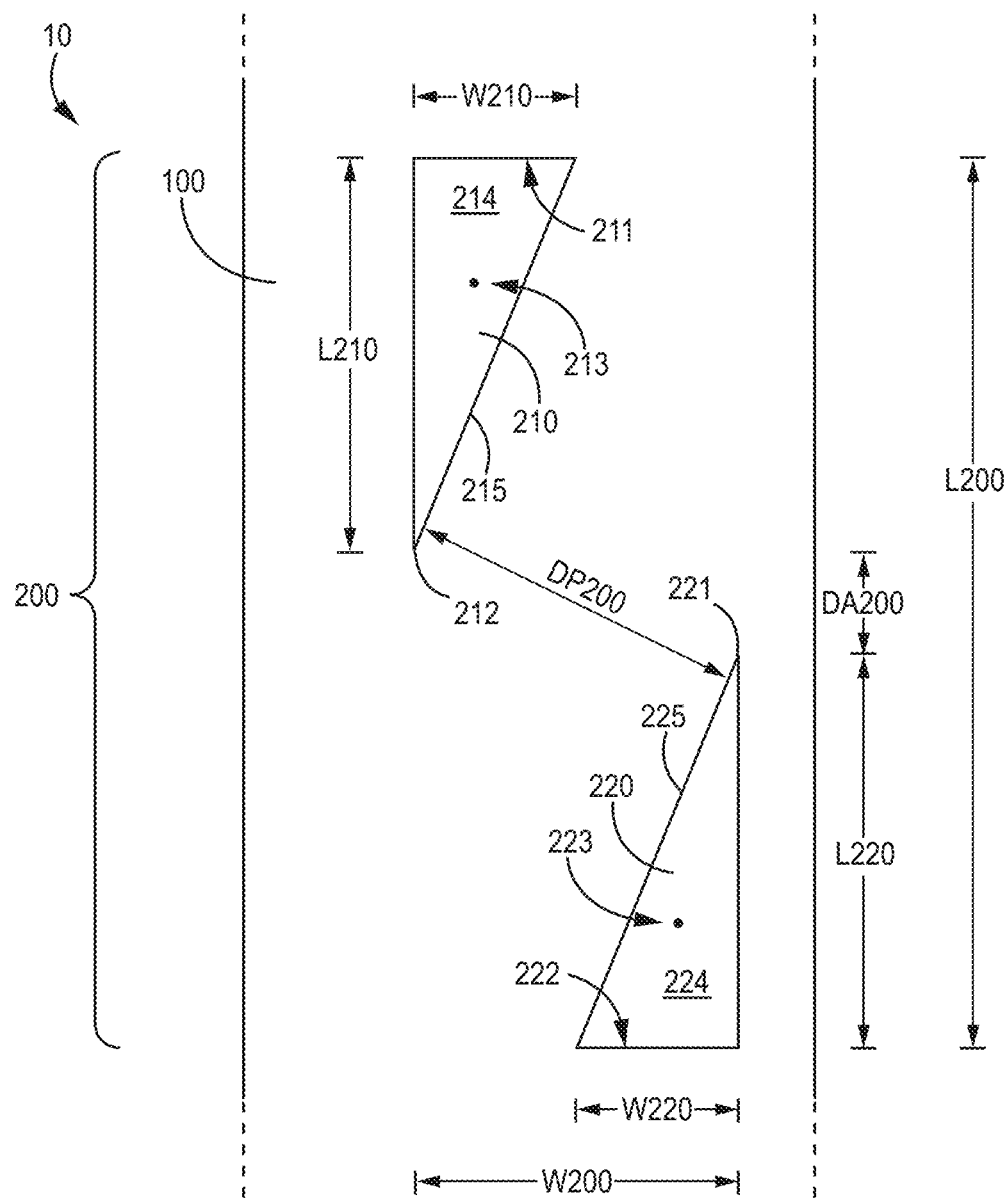
FIG. 5 is an unwrapped side view of the stimulator lead showing the relative placement of imaging markers on the stimulator lead of FIG. 2.

The imaging marker 200 may include one or more marker segments. For example, in some embodiments, the imaging marker 200 includes a first marker segment 210 and a second marker segment 220, such that the first and second marker segments 210, 220 are separate and distinct from one another (e.g., the segments are not connected by marker material and do not touch each other). The first marker segment 210 has a width W210, and a length L210, as shown in FIG. 5, extending from a first proximal end 211 to a first distal end 212, and the second marker segment 220 has a width W220, and a length L220 extending from a second proximal end 221 to a second distal end 222. The imaging marker 200 has an overall length L200 and an overall width W200, both of which include, respectively, the lengths or widths of the first and second marker segments 210, 220 and any gaps between the first and second marker segments 210, 220. These dimensions are shown in FIG. 5, which is an unwrapped two-dimensional (2D) view of the lead as if the cylindrical surface of the lead were "unrolled" and laid out flat. In this view, the entirety of first and second marker segments 210, 220 are simultaneously visible.

The first and second marker segments 210, 220 may be separated from each other in an axial direction along the length of the main body 100 and/or in an angular direction about the circumference of the main body 100. Placement of the first and second marker segments 210, 220 is demonstrated in the exemplary embodiments shown in FIGS. 3A, 3B, 4, and 5.

The first marker segment 210 has a first center point 213 (FIG. 5) and a first marker surface 214 occupying a first arc 270 having angle α270 (FIG. 4) on the main body 100 of the stimulator lead 10. The second marker segment 220 has a second center point 223 and a second marker surface 224 occupying a second arc 280 having angle β280 on the main body 100. The term "center point" is used here to refer to the geometric center (i.e., centroid; arithmetic mean point) of the marker segment surface. If the marker segment surface is triangular (e.g., has a triangle-shaped projection in a longitudinal plane), the geometric center can be determined by finding the intersection of the triangle's medians. According to an embodiment, the first arc 270 and the second arc 280 are separated by an intermediate arc 290, as shown in FIGS. 3A, 3B, and 4.

Figure 3A:
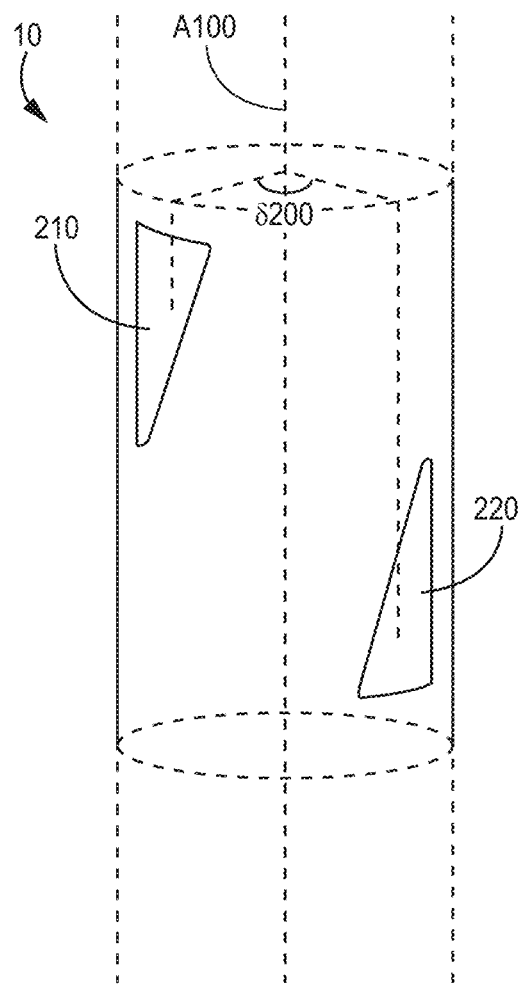
FIGS. 3A and 3B are partial perspective views of the stimulator lead of FIG. 2.
Figure 3B:
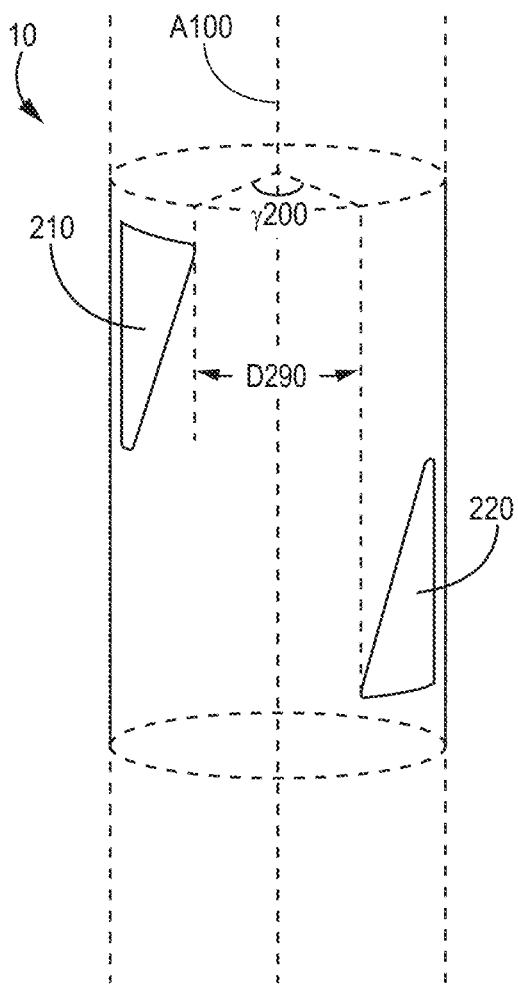
Figure 4:
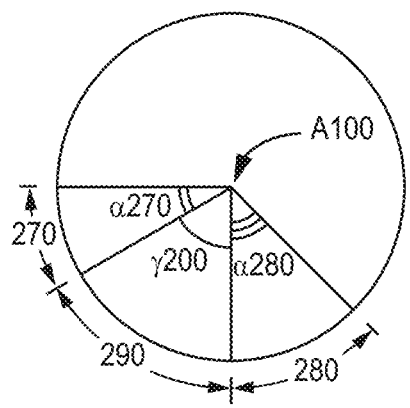
FIG. 4 is a cross-sectional view of the stimulator lead showing the angular placement of imaging markers on the stimulator lead of FIG. 2.

The first center point 213 may be separated from the second center point 223 by a separation angle δ200, as shown in FIG. 3A. The separation angle δ200 may vary between a lower limit and an upper limit, the lower limit being about 95 degrees, about 100 degrees, about 105 degrees, or about 110 degrees, and the upper limit being about 150 degrees, about 145 degrees, about 140 degrees, about 135 degrees, or about 130 degrees.

The intermediate arc 290 separating the first arc 270 and the second arc 280 may also be referred to as the gap between the first marker segment 210 and the second marker segment 220. The gap refers to the distance between the closest points of the first and second marker segments 210, 220 in a lateral direction (perpendicular to the axis A100) along intermediate arc 290, as shown in FIG. 4. The intermediate arc 290 (e.g., gap) may have a gap angle γ200 that may vary between a lower limit and an upper limit, the upper limit being about 65 degrees, about 60 degrees, about 55 degrees, about 50 degrees, or about 45 degrees, and the lower limit being about 0 degrees, about 5 degrees, about 10 degrees, about 15 degrees, about 20 degrees, about 30 degrees, or about 40 degrees. The distance D290 between the first arc 270 and the second arc 280 along the intermediate arc 290 may vary between a lower limit and an upper limit, the lower limit being about 0 mm, 1.0 mm, or 2.0 mm. The upper limit of the distance D290 may be about 5.0 mm, about 4.0 mm, about 3.0 mm, or about 2.0 mm.

In some embodiments, the first and second marker segments 210, 220 are not separated in an angular direction (e.g., the gap angle γ200 is zero degrees and the distance D290 is zero mm), or they may overlap in the angular direction.

FIG. 5 illustrates the first and second marker segments 210, 220 with side edges facing each other that are parallel to one another but at an angle relative to a longitudinal axis. The distance between the first and second marker segments 210, 220 may also be measured as the shortest (perpendicular) distance DP200 from the first side edge 215 of the first marker segment 210 to the second side edge 225 of the second marker segment 220, along the arc of the main body. The distance DP200 may vary between a lower limit and an upper limit. The lower limit of the distance DP200 may be about 2.0 mm, about 2.5 mm, or about 3.0 mm. The upper limit of the distance DP200 may be about 6.0 mm, about 5.0 mm, or about 4.0 mm.

The first and second marker segments 210, 220 may also be separated from each other in an axial direction by a distance DA200. In other words, the first marker segment 210 may have a first axial position along the main body 100, and the second marker segment 220 may have a second axial position along the main body 100 such that the first axial position and the second axial position do not overlap. The axial distance DA200 between the first and second marker segments 210, 220 may vary between a lower limit and an upper limit, the lower limit being about 0 mm, about 1 mm, or about 2 mm, and the upper limit being about 5 mm, about 4 mm, or about 3 mm. In one exemplary embodiment, the axial distance DA200 is about 2 mm. In one embodiment, the first and second marker segments 210, 220 are not separated axially but rather, the first axial position and the second axial position abut each other. In some embodiments, the first and second marker segments 210, 220 may overlap by up to 3 mm, up to 2 mm, or up to 1 mm in the axial direction.

The imaging marker 200 may be sized to provide information about the orientation of the stimulator lead 10 when using any one of the commonly used imaging techniques, such as MRI, CT, X-ray, fluoroscope, or OARM®. The imaging marker 200 may have an overall length L200 that may vary between a lower limit and an upper limit, the lower limit being about 3.0 mm, about 3.5 mm, about 4.0 mm, about 4.5 mm, about 5.0 mm, about 5.5 mm, or about 6.0 mm, and the upper limit being about 12.0 mm, about 11.0 mm, about 10.0 mm, about 9.0 mm, or about 8.0 mm. In one exemplary embodiment, the length L200 of the imaging marker 200 is about 5 to 6 mm. The imaging marker may have an overall width W200 that may vary between a lower limit and an upper limit. The lower limit of the width W200 may be about 2.0 mm, about 2.5 mm, or about 3.0 mm. The upper limit of the width W200 may be up to the circumferential dimension of the stimulator lead 10, such as about 6.0 mm, about 5.0 mm, about 4.5 mm, about 4.0 mm, about 3.5 mm, or about 3.0 mm. The width W200 of the imaging marker 200 is measured along the cylindrical surface that the imaging marker 200 is disposed on, or as if the surface were depicted as a flat surface "peeled" or "unrolled" off of the stimulator lead 10 as shown in FIGS. 6A-6F, width W200 can be measured along that flat surface along a line perpendicular to the longitudinal axis of the lead.

In embodiments where the imaging marker 200 includes a first marker segment 210 and a second marker segment 220, the first and second marker segments 210, 220 may independently have a length L210, L220 that may vary between a lower limit and an upper limit. The lower limit of the length L210, L220 may be about 1.5 mm, about 2.0 mm, about 2.5 mm, or about 3.0 mm. The upper limit of the length L210, L220 may be about 5.0 mm, about 4.5 mm, about 4.0 mm, about 3.5 mm, or about 3.0 mm. The length L210, L220 is measured parallel to the longitudinal axis A100 of the main body 100. The first and second marker segments 210, 220 may also independently have a width W210, W220 that may vary between a lower limit and an upper limit. The lower limit of the width W210, W220 may be about 1.0 mm, about 1.5 mm, about 2.0 mm, or about 2.5 mm. The upper limit of the width W210, W220 may be about 4.0 mm, about 3.5 mm, or about 3.0 mm. The width W210, W220 is measured along the surface 214, 215 in a direction perpendicular to the longitudinal axis A100 of the main body 100.

The first and second marker segments 210, 220 may either be identical in shape, be mirror images of each other, or have different shapes. In one exemplary embodiment, the first marker surface 214 has a first shape, and the second marker surface 224 has a second shape that is the same as the first shape. The second marker surface 224 may be in the same orientation as the first marker surface, or may be rotated to a different orientation. In another exemplary embodiment, the first marker surface 214 has a first shape, and the second marker surface 224 has a second shape that is a mirror image of the first shape. In yet another exemplary embodiment, the first marker surface 214 has a first shape, and the second marker surface 224 has a second shape that is different from the first shape. If the second marker surface 224 has a shape that is the same as or a mirror image of the shape of the first marker surface 214, the shape may be rotated about its center point 223. In the exemplary embodiment shown in FIGS. 3A, 3B, 4, and 5, the second marker surface 224 has a shape that is the same as the first marker surface 214, but is rotated 180 degrees about the center point 223 of the second marker segment 220.

The imaging marker 200 and/or the first and second marker segments 210, 220 may have any suitable shape. The shape of the imaging marker 200 and/or the first and second marker segments 210, 220 is described as the two-dimensional shape of the marker in the unwrapped view, as shown for example, in FIG. 5 and FIGS. 6A-6F. The imaging marker 200 and/or the first and second marker segments 210, 220 may be, for example, rectangular, triangular, or other polygonal shape, either regular or irregular, having either sharp or rounded corners.

Exemplary marker segments 1210, 1220, 200', 2210, 2220, 3210, 3220, 4210, 4220, 210, and 220 usable in the stimulator lead 10 are shown in FIGS. 6A-6F and FIGS. 7A-7F. In one embodiment, one or both of the first and second marker segments 210, 220 individually have a shape that is asymmetrical about any line or point. An exemplary electrode arrangement similar to that in FIG. 2 is shown, with segmented electrodes 142 sandwiched by first and second ring electrodes 141, 143.

Figure 7A:
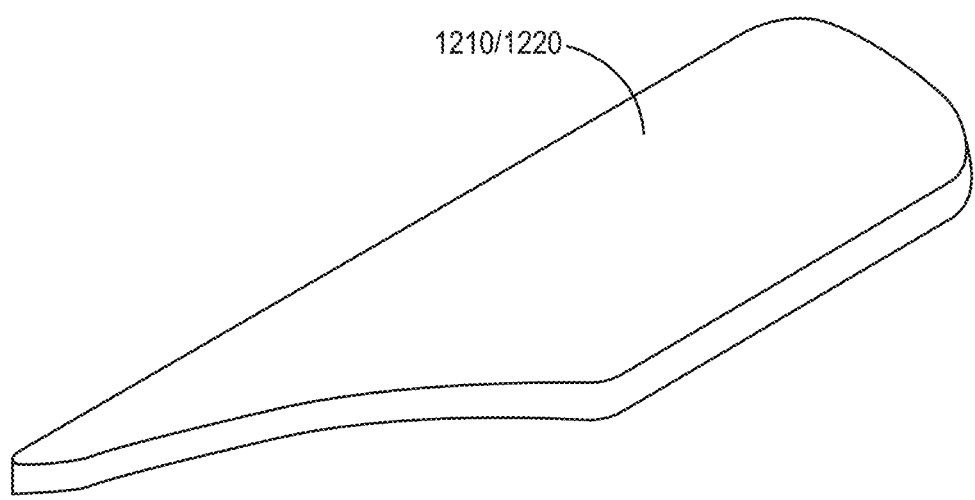
FIGS. 7A-7F are perspective views of imaging markers and marker segments according to embodiments.
Figure 7B:
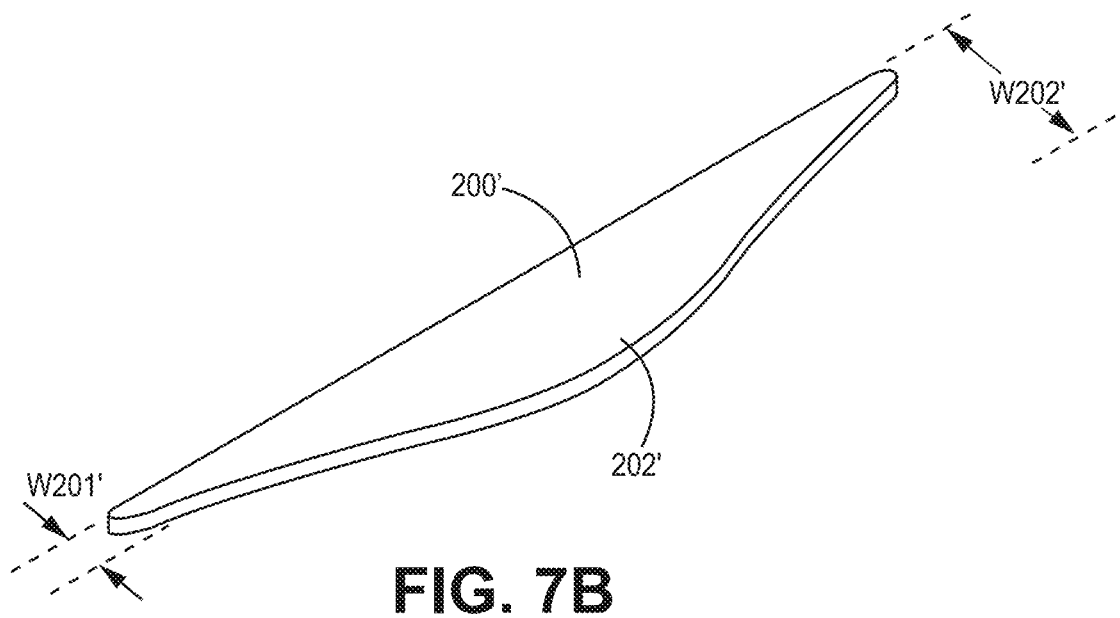
Figure 7C:
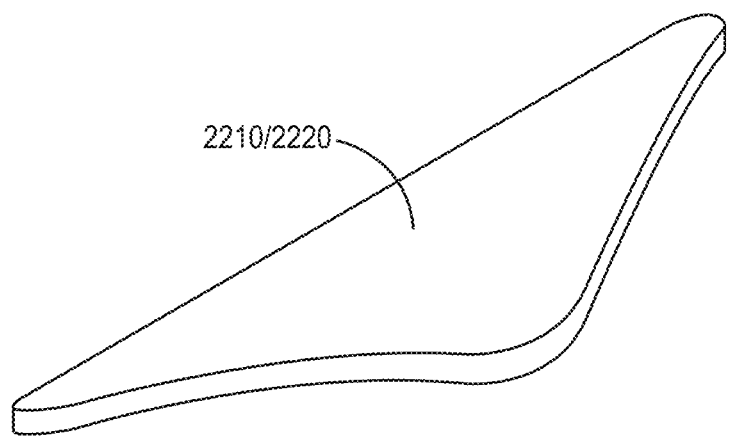
Figure 7D:
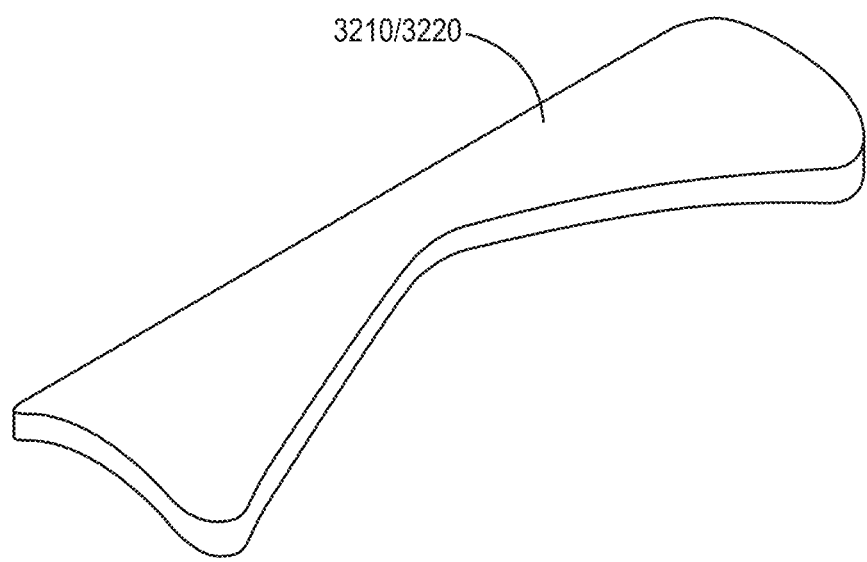
Figure 7E:
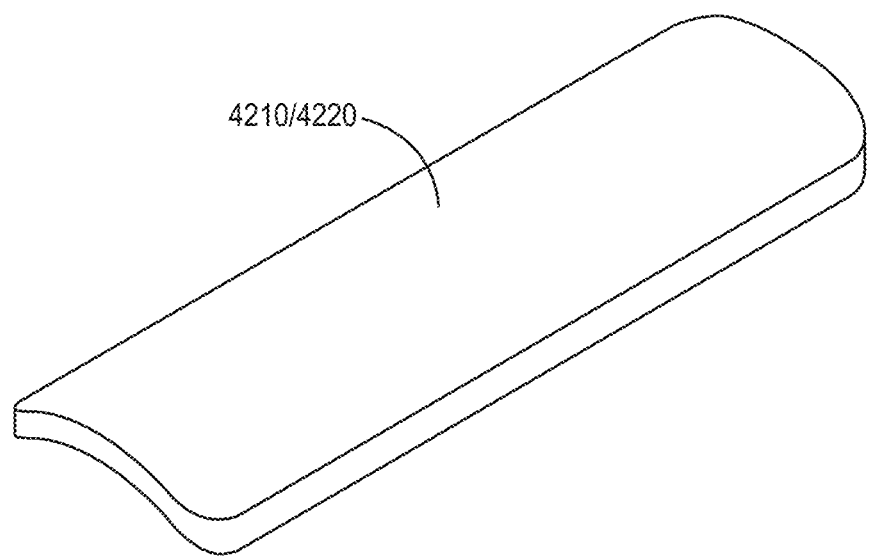
Figure 7F:
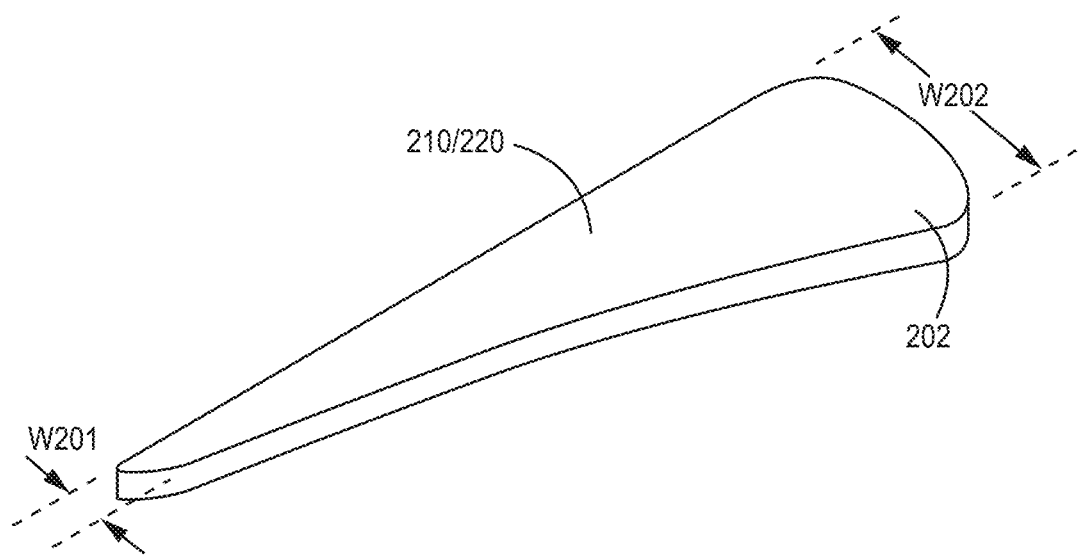

In an embodiment, as shown in FIG. 7F, the imaging marker segment (first marker segment 210 or second marker segment 220) has a first width W201 and a second width W202 such that the second width W202 is greater than the first width W201, creating a lateral protrusion 202 in the shape of the imaging marker segment. For example, the second width W202 may vary between a lower limit and an upper limit, where the lower limit may be about 0.5 mm, about 0.6 mm, or about 0.7 mm, and the upper limit may be about 1.2 mm, about 1.1 mm, or about 1.0 mm. In one exemplary embodiment, the first and second marker segments 210, 220 are triangular in shape. For example, the first and second marker segments 210, 220 may have a triangle-shaped projection in a longitudinal plane (e.g., a plane parallel to the longitudinal axis of the lead body). In one specific embodiment, one or both of the first and second marker segments 210, 220 may be shaped like a right triangle (e.g., with rounded corners), such that the base of the triangle has the second width W202, and the "tip" of the triangle opposite of the base has the first width W201. The base of the first marker segment 210 may be disposed at the proximal end of the first marker segment 210 and the base of the second marker segment 220 at the distal end of the second marker segment 220 (opposite of the base of the first marker segment 210), with the hypotenuse of the first marker segment 210 facing the hypotenuse of the second marker segment 220, as shown in FIG. 2. The first and second marker segments 210, 220 may be separate and distinct, not connected by other parts (e.g., not connected by a connecting member or band) of the imaging marker 200.

The imaging marker 200 and/or the first and second marker segments 210, 220 may have a curved transverse cross section that follows the contour of the cylindrical surface on which the imaging marker 200 and/or the first and second marker segments 210, 220 are disposed.

Figure 6A:
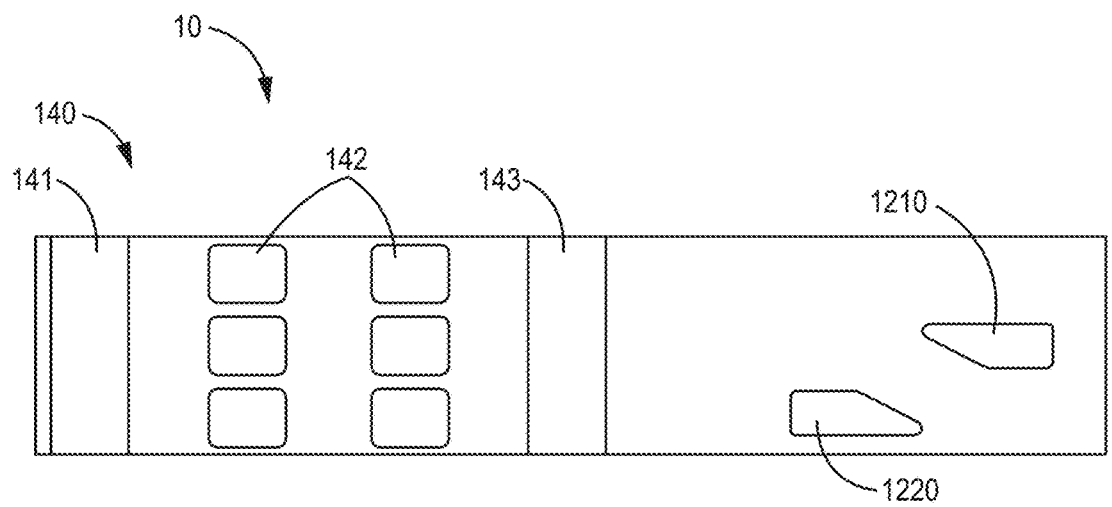
FIGS. 6A-6F are unwrapped side views of layouts of imaging markers on stimulator leads according to embodiments.
Figure 6B:
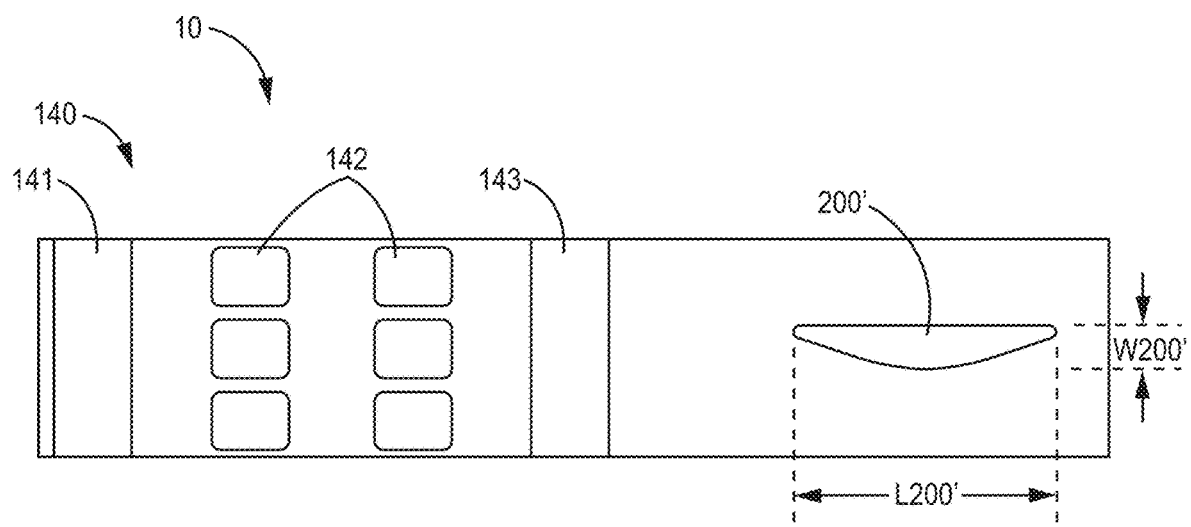
Figure 6C:
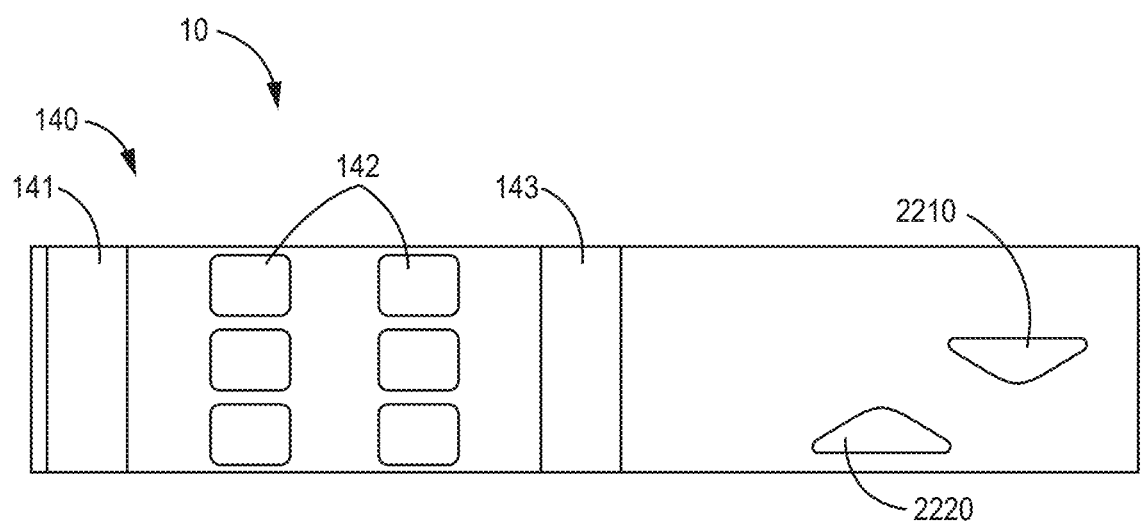
Figure 6D:
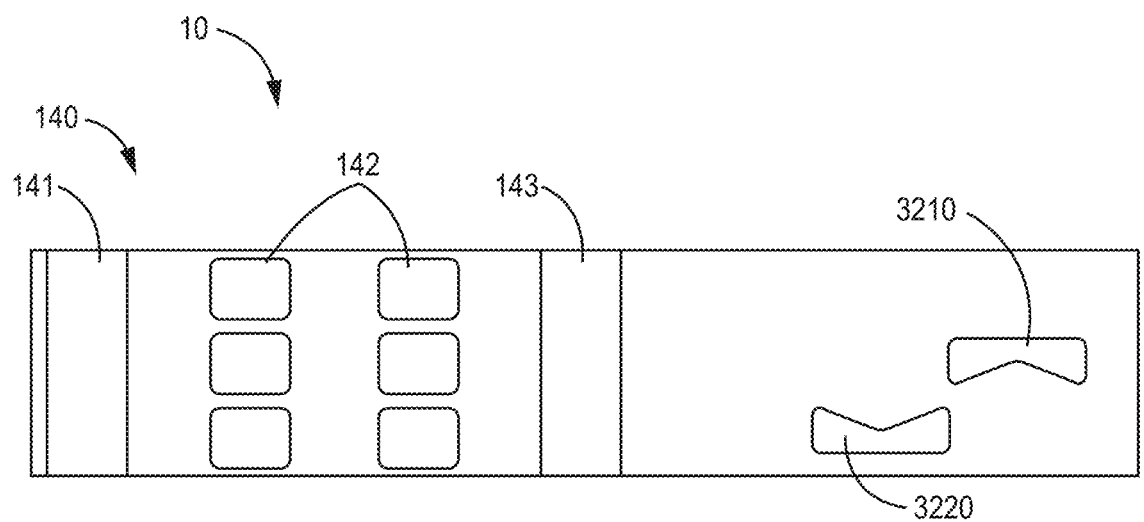
Figure 6E:
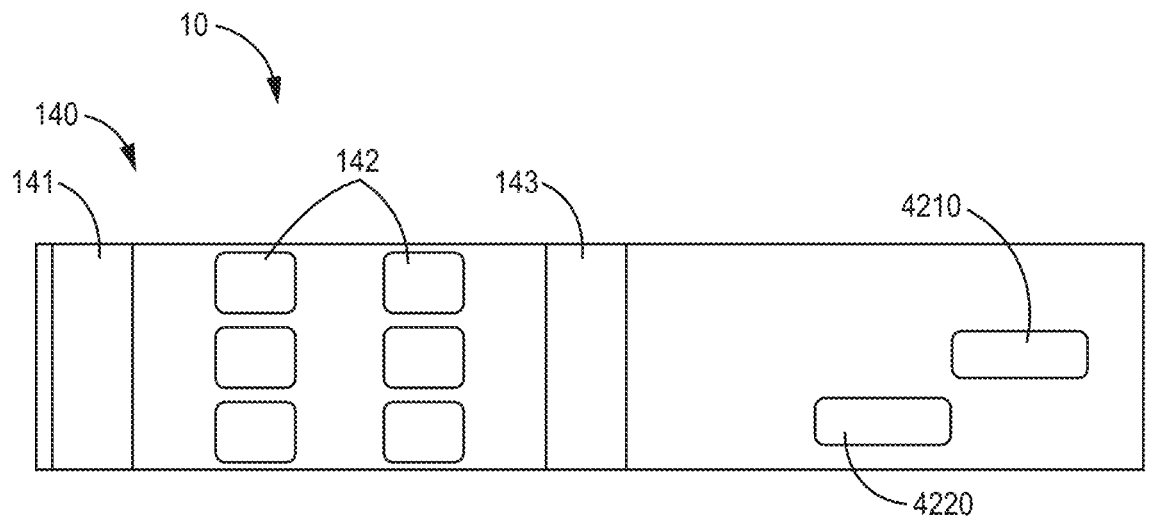
Figure 8:
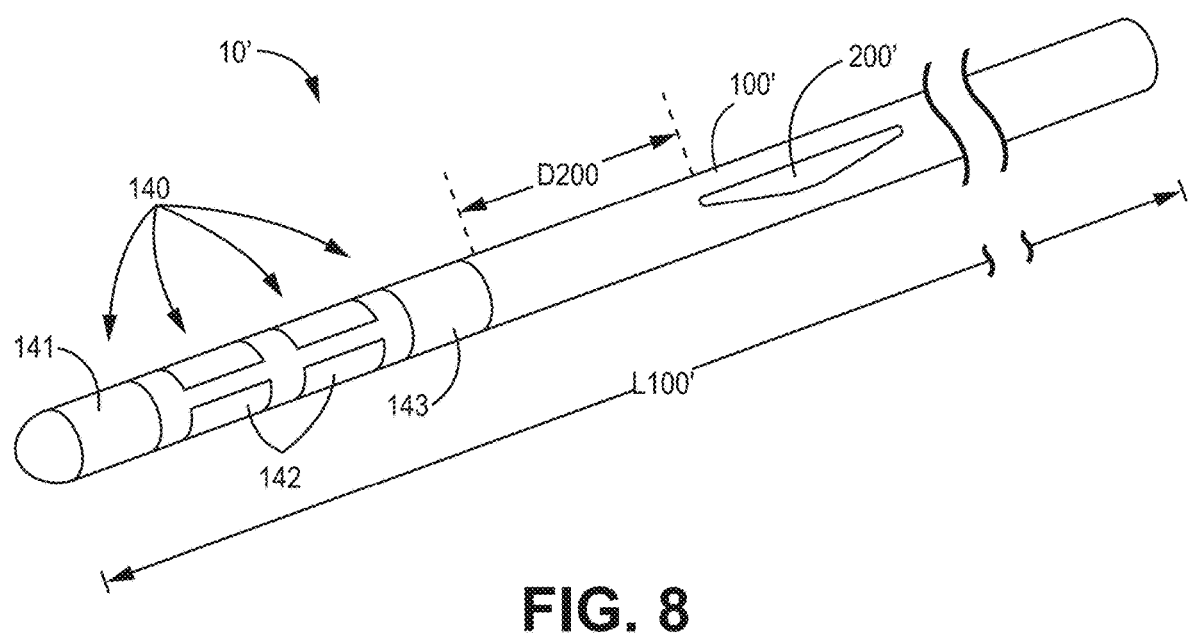
FIG. 8 is a perspective view of a stimulator lead according to an embodiment.
Figure 9A:
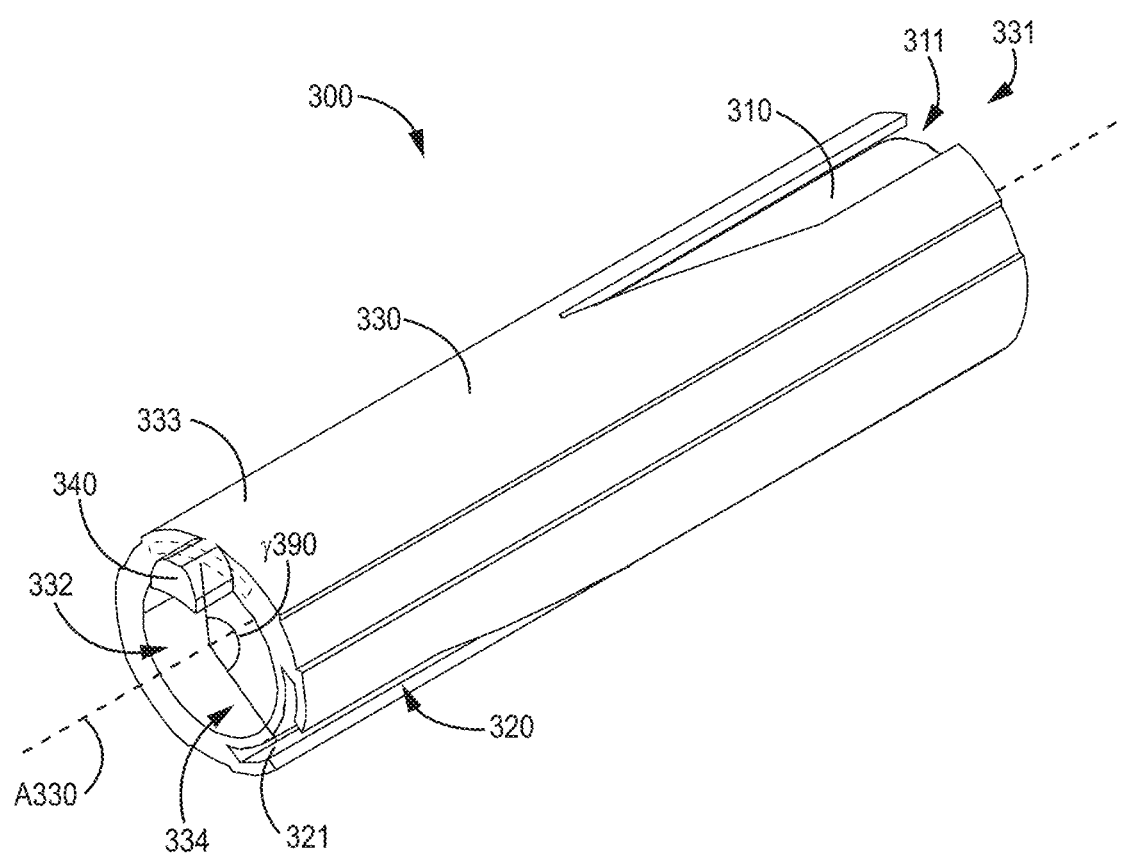
FIG. 9A is a perspective view of a sleeve for a stimulator lead according to an embodiment.
Figure 9B:
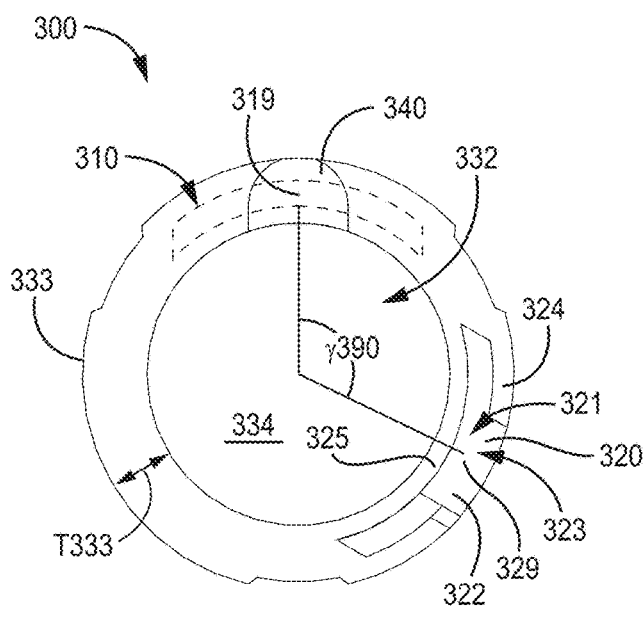
FIG. 9B is a bottom end view of the sleeve of FIG. 9A.
Figure 9C:
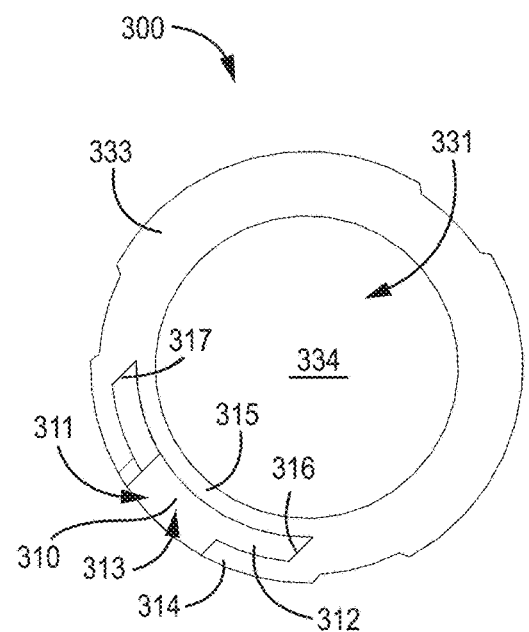
FIG. 9C is a top end view of the sleeve of FIG. 9A.
Figure 9D:
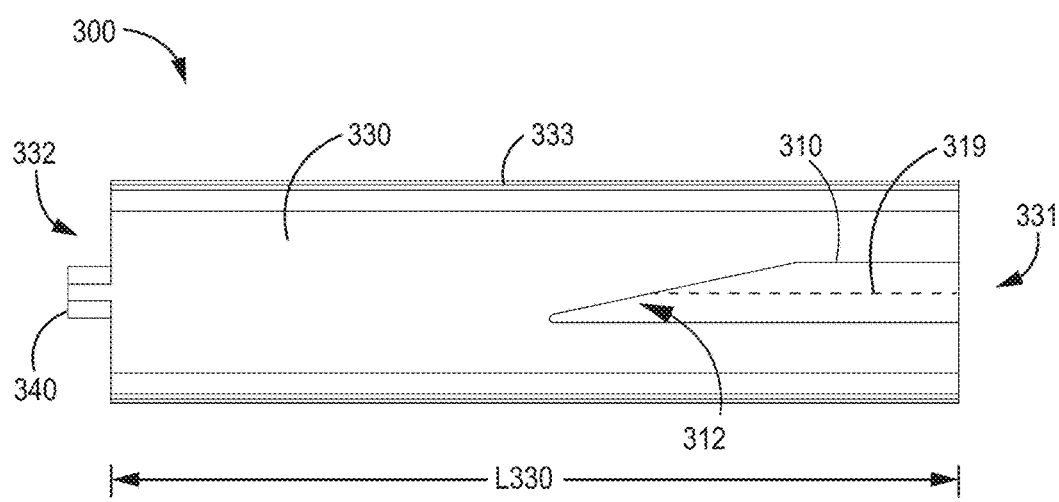
FIG. 9D is a side view of the sleeve of FIG. 9A.
Figure 10A:
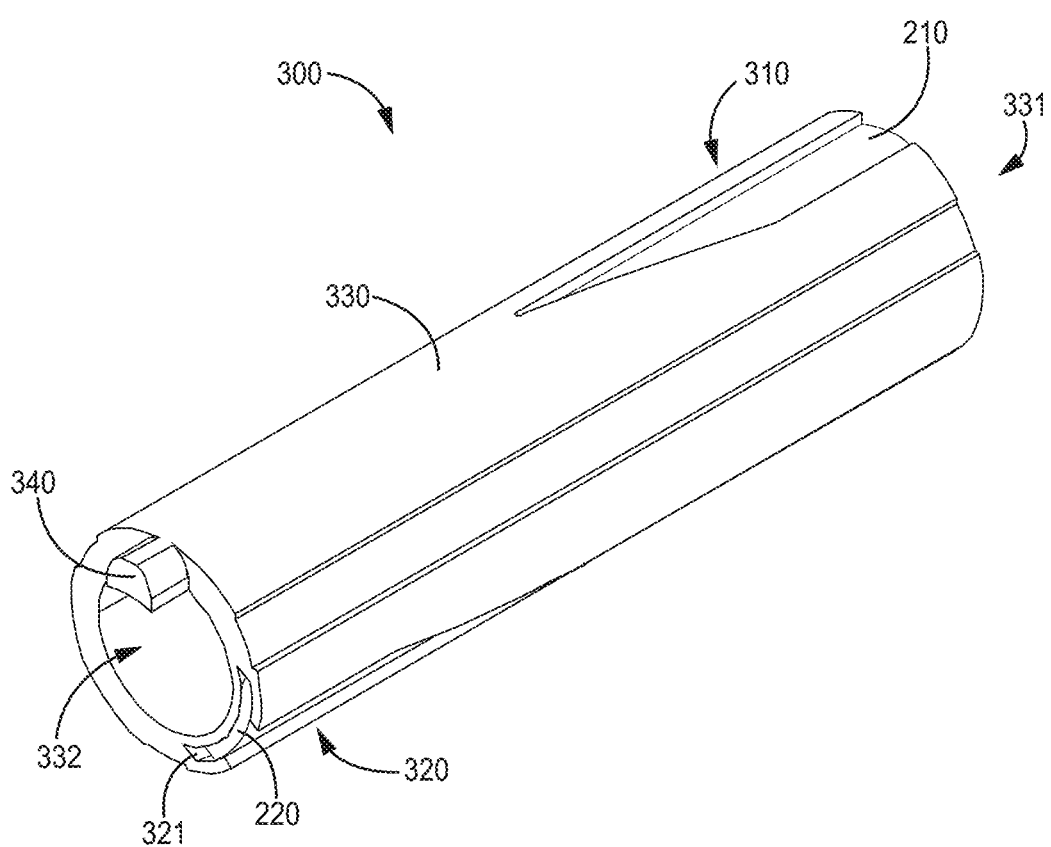
FIG. 10A is a perspective view of a sleeve with an imaging marker for a stimulator lead according to an embodiment.
Figure 10B:
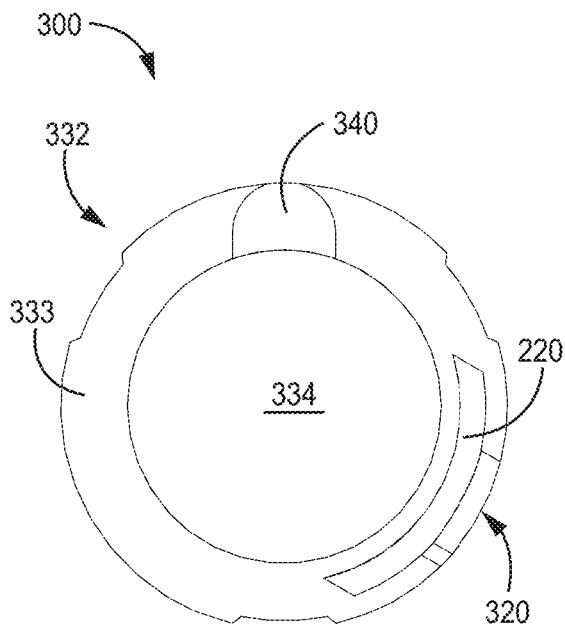
FIG. 10B is a bottom end view of the sleeve of FIG. 10A.
Figure 10C:
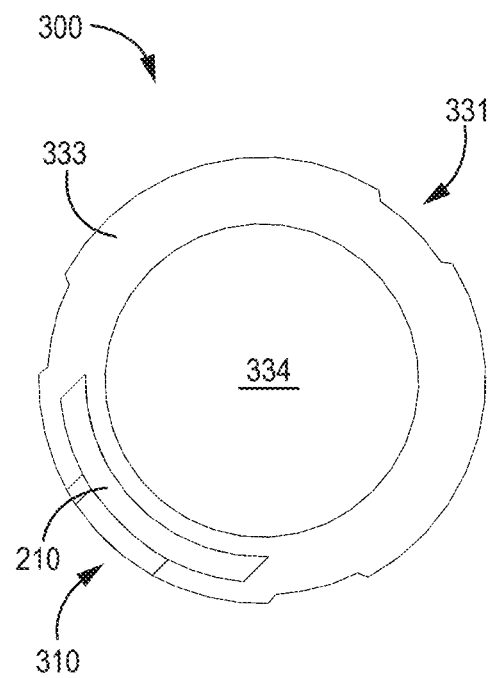
FIG. 10C is a top end view of the sleeve of FIG. 10A.
Figure 10D:
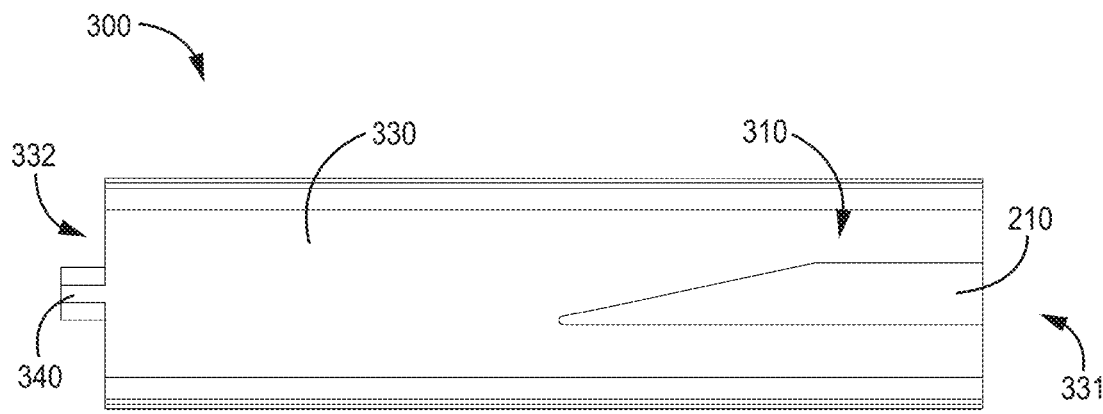
FIG. 10D is a side view of the sleeve of FIG. 10A.

In some embodiments, the medical lead includes a single one-piece imaging marker 200' (FIG. 7B). An exemplary embodiment of such a medical lead is shown in FIG. 6B and FIG. 8. The imaging marker 200' may have a length L200' that may vary between a lower limit and an upper limit, the lower limit being about 3.0 mm, about 3.5 mm, about 4.0 mm, about 4.5 mm, about 5.0 mm, about 5.5 mm, or about 6.0 mm, and the upper limit being about 12.0 mm, about 11.0 mm, about 10.0 mm, about 9.0 mm, or about 8.0 mm. In one exemplary embodiment, the length L200' of the imaging marker 200' is about 5 to 6 mm. The imaging marker may have an overall width W200' that may vary between a lower limit and an upper limit, the lower limit being about 2.0 mm, about 2.5 mm, or about 3.0 mm, and the upper limit being up to the circumferential dimension of the stimulator lead 10, or about 6.0 mm, about 5.0 mm, about 4.5 mm, about 4.0 mm, about 3.5 mm, or about 3.0 mm. The width W200' of the imaging marker 200' is measured along the cylindrical surface that the imaging marker 200' is disposed on, or if the surface were depicted as a flat surface "peeled" or "unrolled" off of the stimulator lead 10 as shown in FIG. 6B, width W200' can be measured along that flat surface.

As illustrated in FIG. 7B, the imaging marker 200' has a first width W201' and a second width W202' such that the second width W202' is greater than the first width W201', creating a lateral protrusion 202' in the shape of the imaging marker 200'.

FIG. 8 demonstrates an example of the single one-piece imaging marker 200' implemented in a stimulator lead 10'. The stimulator lead 10' includes a main body 100' with length L100' and electrodes 140 (e.g., segmented electrodes 142 located between first and second ring electrodes 141, 143) disposed along the length of the main body 100'. The imaging marker 200' is disposed proximally at a distance D200 from the electrodes 140.

In some embodiments, the imaging marker 200 and/or the first and second marker segments 210, 220 are disposed in or on a carrier or sleeve 300. FIGS. 9A-9D show exemplary embodiments of the sleeve 300. The sleeve may at least partially surround the main body 100 and may be used to axially and radially position the imaging marker 200 on the main body 100 and to hold the imaging marker 200 in place. The sleeve 300 may include one or more pockets (e.g., a first pocket 310 and a second pocket 320) for receiving the imaging marker 200 or the first and second marker segments 210, 220.

The sleeve 300 includes a tubular body 330 having a first open end 331 and a second open end 332. The sleeve 300 has a tubular wall 333 extending between the first and second ends 331, 332, defining a hollow center 334. A longitudinal axis A330 extends through the hollow center 334 of the tubular body 330. In the exemplary embodiment shown in FIGS. 9A-9D, the sleeve 300 includes a first pocket 310 and a second pocket 320. The first pocket 310 is disposed in the tubular wall 333 having a thickness T333, and has a first access opening 311 at the first open end 331 of the tubular body 330. The first pocket 310 has a front side 314 (FIG. 9C) facing an outside of the tubular body 330 and a back side 315 facing the hollow center 334. The second pocket 320 has a front side 324 (FIG. 9B) facing an outside of the tubular body 330 and a back side 325 facing the hollow center 334. The front sides 314, 324 of the first and second pockets 310, 320 may be partially open. The first and second pockets 310, 320 have a curved transverse cross section with an arc about the longitudinal axis of the tubular body.

The size and shape of the first pocket 310 may be constructed to receive an imaging marker, such as the first marker segment 210. The first pocket 310 may define a cavity 313 having a first side 316 and a second side 317, the cavity 313 extending in an axial direction from the first access opening 311 to the bottom 312 of the first pocket 310. The size and shape of the first pocket 310 may be constructed to reflect the size and shape of the first marker segment 210. For example, the pocket may have a length between the first access opening 311 and the bottom 312 that reflects the length of the marker segment, a width between the first and second sides 316, 317 that reflects the width of the marker segment, and a curvature that reflects the curvature of the marker segment. In one embodiment, at least a portion of the second side 317 is disposed at an angle relative to the first side 316.

The sleeve 300 may include a second pocket 320 also disposed in the tubular wall 333 and having a second access opening 321 at the second open end 332 of the tubular body 330. The second pocket 320 define a cavity 323 extending from the first access opening 321 to the bottom 322 of the pocket. The size and shape of the second pocket 320 may similarly reflect the size and shape of the second marker segment 220.

In some embodiments, the first pocket 310 is sized to receive a first marker segment 210 and the second pocket 320 is sized to receive a second marker segment 220. FIGS. 10A-10D show the sleeve with the first and second marker segments 210, 220 inserted in the first and second pockets 310, 320. In the event that the first and second marker segments 210, 220 have the same size and shape, the second pocket 320 may also have the same size and shape as the first pocket 310, and may differ only in its placement on the tubular body 330 of the sleeve 300.

According to some embodiments, the first pocket 310 has a first longitudinal center line 319 (see FIGS. 9A-9D) and the second pocket 320 has a second longitudinal center line 329 separated from the first longitudinal center line 319 by an angle γ390 that may vary between a lower limit and an upper limit. The lower limit being of angle γ390 may be about 95 degrees, about 100 degrees, about 105 degrees, or about 110 degrees, and the upper limit about 150 degrees, about 145 degrees, about 140 degrees, about 135 degrees, or about 130 degrees about the longitudinal axis of the tubular body 330.

The sleeve 300 may be sized to fit on or over the main body 100 of the medical lead. The sleeve 300 may further include an orientation protrusion 340 extending axially from one of the first and second open ends 331, 332. The orientation protrusion 340 can be used to orient the sleeve 300 on the main body 100 during manufacturing of the stimulator lead 10.

The sleeve 300 and/or the first and second marker segments 210, 220 may be further covered by an electrically insulating layer 400. The electrically insulating layer 400 may be, for example, an overmold 410 of a polymeric material. The overmold 410 may be applied over the sleeve only, or over the whole main body 100. Examples of suitable polymeric materials for the electrically insulating layer 400 include, but are not limited to, polyurethane and polyether ether ketone ("PEEK"). In one embodiment, the overmold 410 is made from polyurethane with 55 D, 75 D, or 80 A durometer (hardness).

Figure 11A:
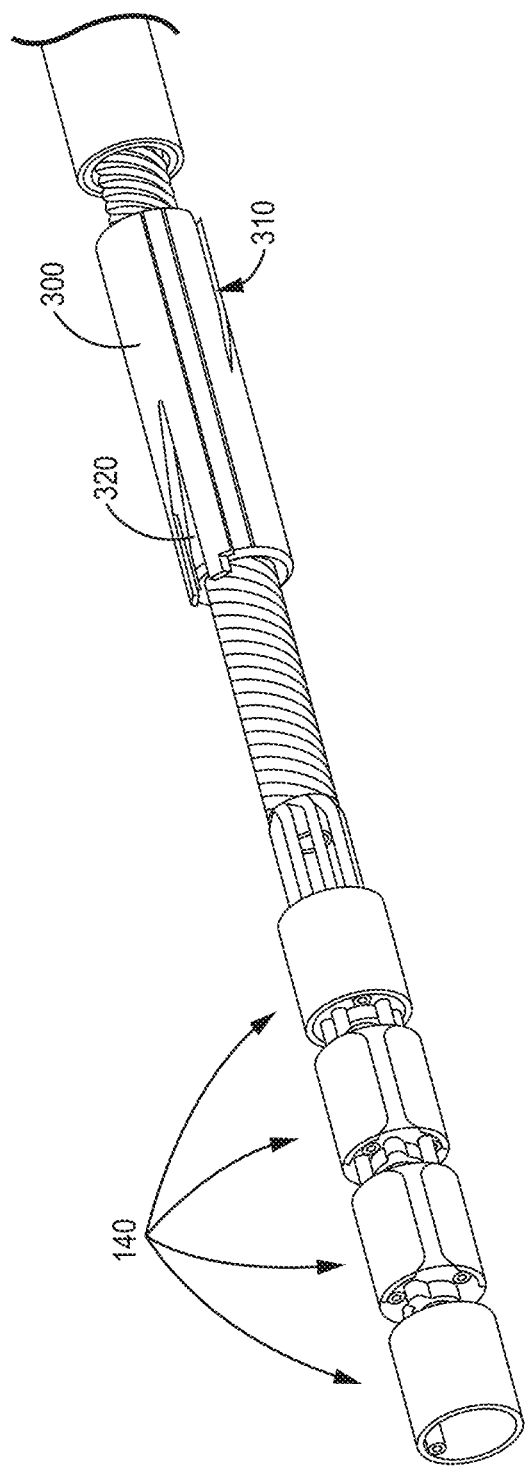
FIG. 11A shows a stimulator lead with a sleeve, without an overmold, according to an embodiment.
Figure 11B:
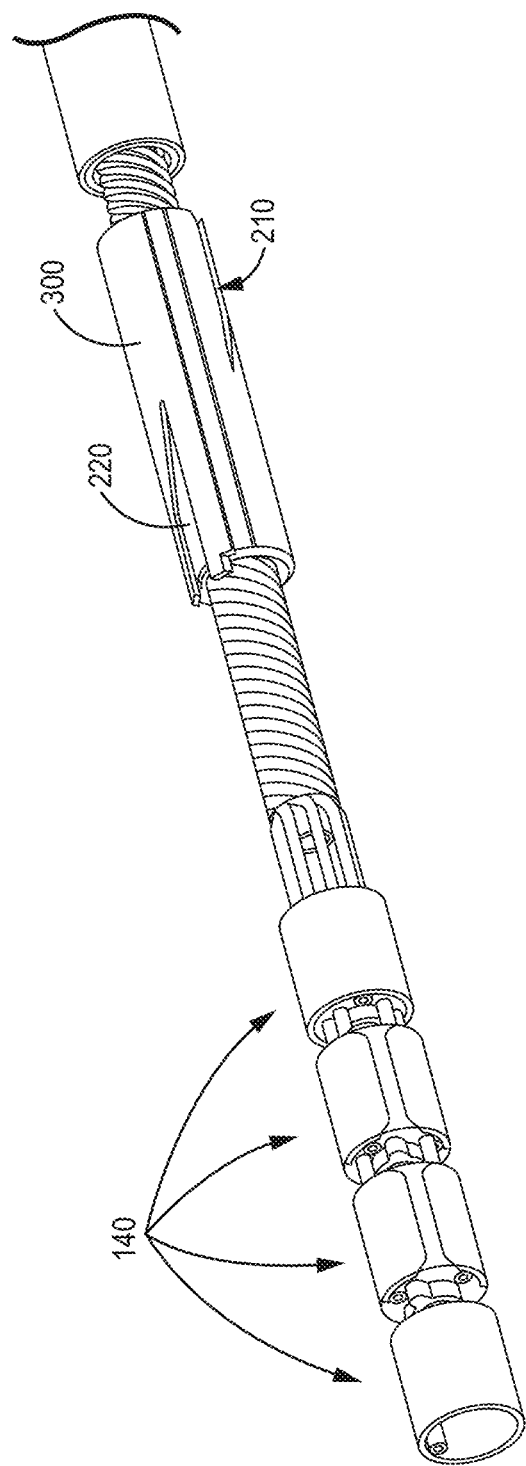
FIG. 11B shows the stimulator lead of FIG. 11A with an imaging marker.
Figure 11C:
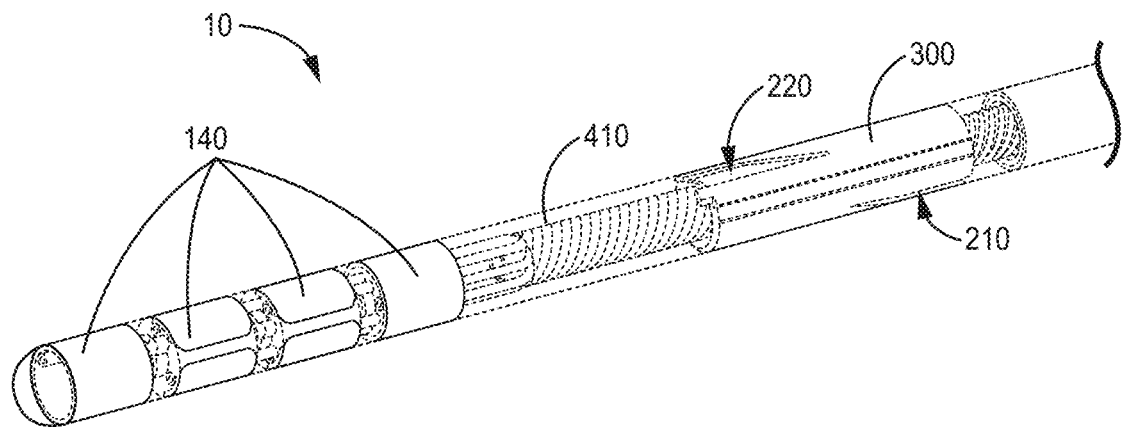
FIG. 11C shows the stimulator lead of FIG. 11B with the overmold in phantom.
Figure 11D:
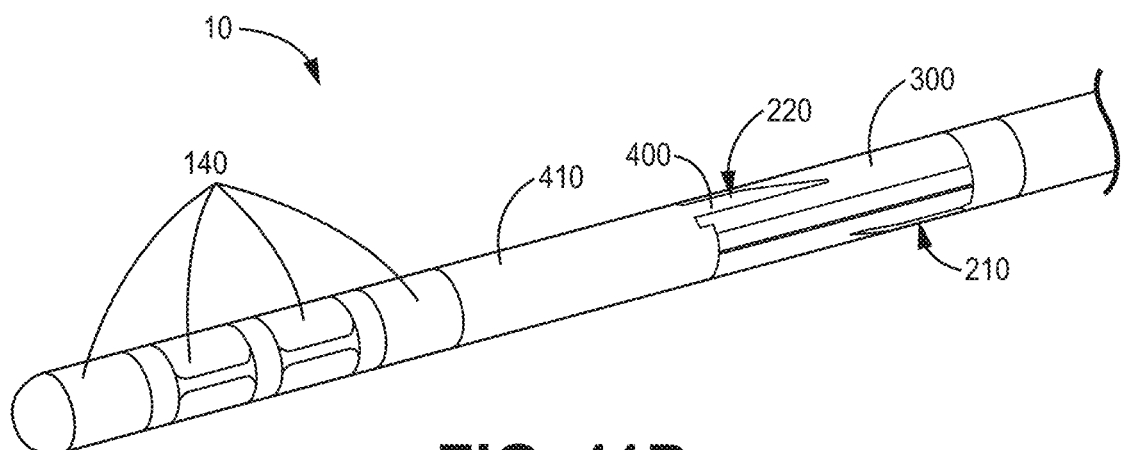
FIG. 11D shows the stimulator lead of FIG. 11B with the overmold.

FIGS. 11A-11D show a stimulator lead 10 in various stages of manufacturing. FIGS. 11A and 11B show parts of the main body, including the electrodes 140 and the electrical connections, and the sleeve 300 placed on the lead. FIG. 11B also includes first and second marker segments 210, 220 inserted in the first and second pockets 310, 320 of the sleeve 300. FIG. 11C shows an overmold 410 in phantom. FIG. 11D shows a finished stimulator lead 10, where the overmold 410 covers the first and second marker segments 210, 220 while leaving the electrodes 140 exposed.

EXAMPLES

Example 1

Stimulator leads with imaging markers were prepared according to embodiments of the present disclosure. The ability to detect the angular orientation of the leads evaluated by a simulation.

The imaging characteristics of six different maker designs and two comparative designs were evaluated by simulating the image of the markers in slices taken along the lead, perpendicular to the lead axis. Markers M1 and M2 were single imaging markers having a shape as shown in FIGS. 7E and 7B (also shown in FIG. 6B), respectively. Markers M3-M6 were two-part markers with shapes and placement corresponding to FIGS. 6C-6F, respectively. The comparative markers C1 and C2 were hooped markers, each with two ring-shaped hoops extending all the way around the lead body and connected by a member extending axially between the two hoops on one side of the lead body. The first comparative marker C1 had a triangular connecting member and the second comparative marker C2 had a rectangular connecting member.

The markers were given an anisotropy rating of low, medium, or high based on the difference in the images along the marker and whether the difference could be used to detect the angular orientation of the lead. The results are shown in TABLE 1 below.

TABLE 1

Imaging Marker Shape Anisotropy Simulation.

| Marker | Marker Type | Anisotropy Rating |
|---|---|---|
| M1 | Single marker, rectangular | Low |
| M2 | Single marker, triangular | Medium |
| M3 | Dual marker, triangular | High |
| M4 | Dual marker, irregular pentagonal | Medium |
| M5 | Dual marker, rectangular | Medium |
| M6 | Dual marker, triangular | High |
| C1 | Hooped marker, triangular connecting member | Low |
| C2 | Hooped marker, rectangular connecting member | Low |

Example 2

Figure 6F:
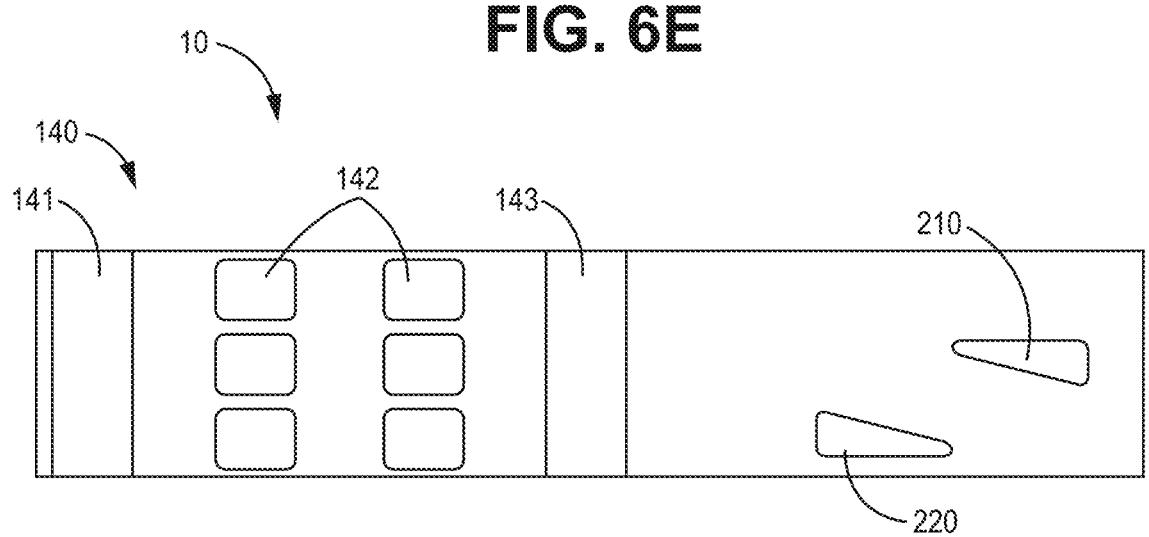
Figure 12:
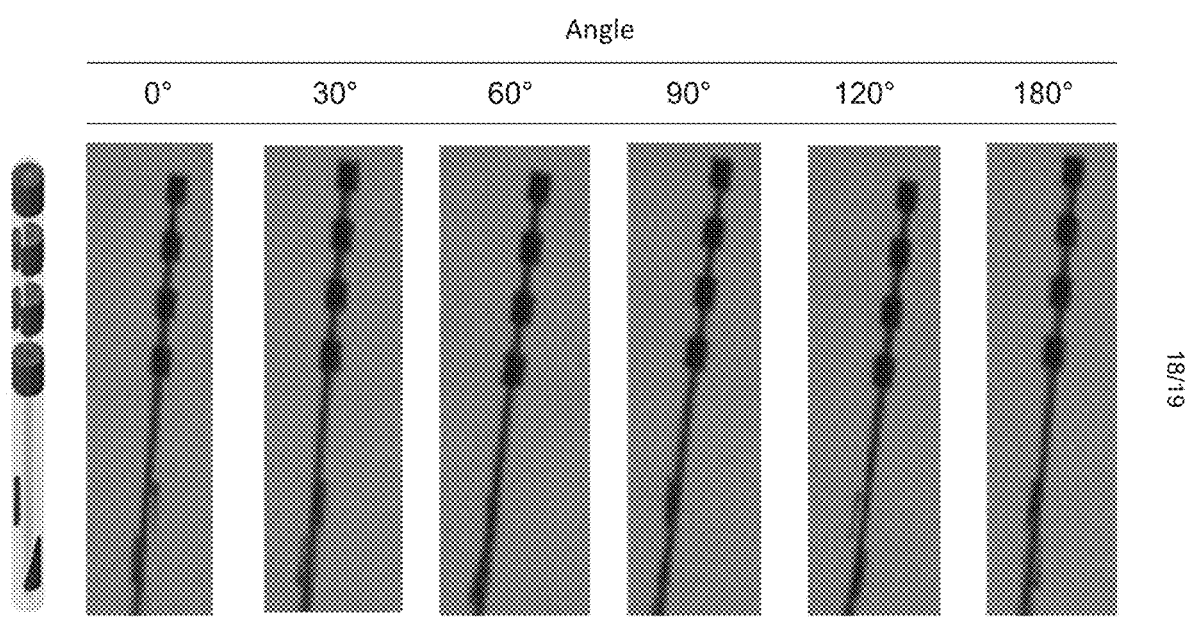
FIG. 12 shows the results of Example 2.

A stimulator lead with an imaging marker according to the design shown in FIG. 6F was prepared with 90/10 platinum/iridium cables, and 90/10 platinum/iridium markers placed in a cavity that retained the markers in place on the stimulator lead. Images of the stimulator lead were recorded using fluoro-imaging as the lead was rotated along its longitudinal axis. The images of the lead at various angles are shown in FIG. 12.

It was observed that using the imaging marker design of FIG. 6F, the orientation of the stimulator lead could be detected in a scan taken along the axis of the lead.

EXEMPLARY EMBODIMENTS

Embodiment 1 is a medical lead comprising: a main body having a length extending from a proximal end to a distal end, a longitudinal axis parallel to the length, and a proximal portion adjacent to the proximal end and a distal portion adjacent to the distal end; a plurality of electrodes defining an electrode region positioned on the main body in the distal portion; and an imaging marker positioned between the electrode region and the proximal end and separated from the electrode region by a distance in an axial direction, the imaging marker comprising a first marker segment and a second marker segment, the first marker segment defining a first center point and a first marker surface occupying a first arc on the main body, the second marker segment defining a second center point and a second marker surface occupying a second arc on the main body separated from the first arc by an intermediate arc, the second center point being radially separated by about 100 to about 145 degrees from the first center point.

Embodiment 2 is the medical lead of embodiment 1, wherein the first and second center points are radially separated by about 105 to about 130 degrees.

Embodiment 3 is the medical lead of any of the previous embodiments, wherein the intermediate arc has an angle up to about 60 degrees.

Embodiment 4 is the medical lead of embodiment 3, wherein the angle is from about 10 degrees to about 35 to about 55 degrees.

Embodiment 5 is the medical lead of any of the previous embodiments, wherein the distance between the imaging marker and the electrode region is at least 3.0 mm.

Embodiment 6 is the medical lead of any of the previous embodiments, wherein the distance between the imaging marker and the electrode region is about 4.0 mm or greater.

Embodiment 7 is the medical lead of any of the previous embodiments, wherein the first marker segment has a distal end and the second marker segment has a proximal end positioned axially within about 2 mm from the distal end of the first marker.

Embodiment 8 is the medical lead of any of the previous embodiments, wherein the first marker segment has a first axial position along the main body and the second marker segment has a second axial position along the main body, and wherein the first axial position and the second axial position do not overlap.

Embodiment 9 is the medical lead of embodiment 8, wherein first axial position and the second axial position abut each other.

Embodiment 10 is the medical lead of any of the previous embodiments, wherein the imaging marker is disposed along a cylindrical surface coaxial with the longitudinal axis of the main body.

Embodiment 11 is the medical lead of embodiment 10, wherein the first marker segment comprises a first side edge closest to the second marker segment, and the second marker segment comprises a second side edge closest to the first marker segment, and wherein first side edge and the second side edge are from about 0.5 mm to about 2.5 mm apart as measured along the intermediate arc.

Embodiment 12 is the medical lead of any of the previous embodiments, wherein the first marker surface has a first shape, and the second marker surface has a second shape that is a mirror image of the first shape.

Embodiment 13 is the medical lead of any of the previous embodiments, wherein the first marker surface has a first shape, and the second marker surface has a second shape that is different from the first shape.

Embodiment 14 is the medical lead of any of the previous embodiments, wherein one or both of the first and second marker segments have a length of about 1 mm to about 4 mm parallel to the longitudinal axis of the main body.

Embodiment 15 is the medical lead of any of the previous embodiments, wherein the imaging marker has a length of about 2 mm to about 8 mm parallel to the longitudinal axis of the main body.

Embodiment 16 is the medical lead of any of the previous embodiments, wherein one or both of the first and second marker segments have a triangle-shaped projection in a longitudinal plane.

Embodiment 17 is the medical lead of any of the previous embodiments, wherein one or both of the first and second marker segments individually have a projection in a longitudinal plane that is asymmetrical about any line or point.

Embodiment 18 is the medical lead of any of the previous embodiments, wherein the imaging marker is radio opaque.

Embodiment 19 is the medical lead of any of the previous embodiments further comprising a sleeve at least partially surrounding the main body and comprising pockets for receiving the first and second marker segments.

Embodiment 20 is the medical lead of any of the previous embodiments, wherein the first and second marker segments are covered by an electrically insulating layer.

Embodiment 21 is the medical lead of any of the previous embodiments, wherein the plurality of electrodes comprises segmented electrodes.

Embodiment 22 is a medical lead comprising: a main body having a length extending from a proximal end to a distal end, a longitudinal axis parallel to the length, and a proximal portion adjacent to the proximal end and a distal portion adjacent to the distal end; a plurality of electrodes defining an electrode region positioned on the main body in the distal portion; and an imaging marker positioned between the electrode region and the proximal end and separated from the electrode region by at least 3.0 mm in an axial direction, and at least partially surrounding the main body and occupying an arc of about 50 to about 90 degrees on the main body, the arc being perpendicular to the longitudinal axis of the main body.

Embodiment 23 is the medical lead of embodiment 22, wherein the imaging marker has a length parallel to the longitudinal axis of the main body and a first width and a second width greater than the first width as measured along the arc, the second width being from about 0.7 mm to about 1.0 mm.

Embodiment 24 is a sleeve for a medical lead, the sleeve comprising: a tubular body having a first open end and a second open end, a tubular wall extending between the first and second ends and defining a hollow center, and a longitudinal axis extending through the hollow center; and a first pocket disposed in the tubular wall and having a curved transverse cross section and a first access opening at the first open end of the tubular body.

Embodiment 25 is the sleeve of embodiment 24, wherein the pocket comprises a front side facing an outside of the tubular body and a back side facing the hollow center, and wherein the front side is partially open.

Embodiment 26 is the sleeve of any of the previous embodiments, wherein the curved transverse cross section of the pocket has an arc about the longitudinal axis of the tubular body.

Embodiment 27 is the sleeve of any of the previous embodiments, wherein the first pocket is sized to receive an imaging marker.

Embodiment 28 is the sleeve of any of the previous embodiments, wherein the first pocket comprises a cavity having a first side and a second side, each side extending from the first access opening to a bottom of the pocket, wherein at least a portion of the second side is disposed at an angle relative to the first side.

Embodiment 29 is the sleeve of any of the previous embodiments further comprising a second pocket disposed in the tubular wall and having a second access opening at the second open end of the tubular body.

Embodiment 30 is the sleeve of embodiment 29, wherein the first pocket has a first longitudinal center line and the second pocket has a second longitudinal center line separated from the first longitudinal center line by about 100 to about 140 degrees about the longitudinal axis of the tubular body.

Embodiment 31 is the sleeve of embodiment 29, wherein the first pocket is sized to receive a first imaging marker and the second pocket is sized to receive a second imaging marker.

Embodiment 32 is the sleeve of any of the previous embodiments, wherein the sleeve is sized to fit over a body of the medical lead.

Embodiment 33 is the sleeve of any of the previous embodiments further comprising an orientation protrusion extending axially from one of the first and second open ends.

Embodiment 34 is a system for stimulating tissue, the system comprising: an implantable medical device; and a medical lead operatively connected to the implantable medical device, the medical lead comprising: a main body having a length extending from a proximal end to a distal end, a longitudinal axis parallel to the length, and a proximal portion adjacent to the proximal end and a distal portion adjacent to the distal end; a plurality of electrodes defining an electrode region positioned on the main body in the distal portion; and an imaging marker positioned between the electrode region and the proximal end and separated from the electrode region by a distance in an axial direction, the imaging marker comprising a first marker segment and a second marker segment, the first marker segment defining a first center point and a first marker surface occupying a first arc on the main body, the second marker segment defining a second center point and a second marker surface occupying a second arc on the main body separated from the first arc by an intermediate arc, the second center point being radially separated by about 100 to about 145 degrees from the first center point.

Embodiment 35 is the system of embodiment 34, wherein the intermediate arc has an angle up to about 60 degrees.

Embodiment 36 is the system of any of the previous embodiments, wherein the distance between the imaging marker and the electrode region is at least 3.0 mm.

Embodiment 37 is the system of any of the previous embodiments, wherein the first marker segment has a distal end and the second marker segment has a proximal end positioned axially within about 2 mm from the distal end of the first marker.

Embodiment 38 is the system of any of the previous embodiments, wherein one or both of the first and second marker segments individually have a projection in a longitudinal plane that is asymmetrical about any line or point.

Embodiment 39 is the system of any of the previous embodiments, wherein the imaging marker is radio opaque.

Various embodiments of the invention have been described. These and other embodiments are within the scope of the following claims.

The invention claimed is:

1. A sleeve for a medical lead, the sleeve comprising: a tubular body having a first open end and a second open end, a tubular wall extending between the first and second ends and defining a hollow center, and a longitudinal axis extending through the hollow center; and a first pocket disposed in the tubular wall and having a curved transverse cross section and a first access opening at the first open end of the tubular body, the first pocket being sized to receive an imaging marker.

2. The sleeve according to claim 1, wherein the first pocket comprises a front side facing an outside of the tubular body and a back side facing the hollow center, and wherein the front side is partially open.

3. The sleeve according to claim 1, wherein the curved transverse cross section of the pocket has an arc about the longitudinal axis of the tubular body.

4. The sleeve of according to claim 1, wherein the first pocket comprises a cavity having a first side and a second side, each side extending from the first access opening to a bottom of the pocket, wherein at least a portion of the second side is disposed at an angle relative to the first side.

5. The sleeve according to claim 1, further comprising a second pocket disposed in the tubular wall and having a second access opening at the second open end of the tubular body.

6. The sleeve according to claim 5, wherein the first pocket has a first longitudinal center line and the second pocket has a second longitudinal center line separated from the first longitudinal center line by about 100 to about 140 degrees about the longitudinal axis of the tubular body.

7. The sleeve according to claim 5, wherein the first pocket is sized to receive a first imaging marker and the second pocket is sized to receive a second imaging marker.

8. The sleeve according to claim 1, wherein the sleeve is sized to fit over a body of the medical lead.

9. The sleeve according to claim 1, further comprising an orientation protrusion extending axially from one of the first and second open ends.

10. A medical lead system, comprising:
  a medical lead comprising:
    a main body having a length extending from a proximal end to a distal end, a longitudinal axis parallel to the length, and a proximal portion adjacent to the proximal end and a distal portion adjacent to the distal end;
    a plurality of electrodes defining an electrode region positioned on the main body in the distal portion; and
  the sleeve according to claim 1, wherein the sleeve is configured to slide over the main body of the medical lead and be disposed about the main body and adjacent to the electrode region.

11. The medical system of claim 10, wherein the distance between the sleeve and the electrode region is at least 3.0 mm.

12. The medical system of claim 10, wherein the plurality of electrodes comprises segmented electrodes.

13. A sleeve for a medical lead, the sleeve comprising:
  a tubular body having a first open end and a second open end, a tubular wall extending between the first and second ends and defining a hollow center, and a longitudinal axis extending through the hollow center;
  a first pocket disposed in the tubular wall and having a curved transverse cross section and a first access opening at the first open end of the tubular body, wherein a first inactive imaging marker is slidably received in the first pocket; and
  a second pocket disposed in the tubular wall and having a second access opening at the second open end of the tubular body, wherein a second inactive imaging marker is slidably received in the second pocket;
  wherein the first pocket has a first longitudinal center line and the second pocket has a second longitudinal center line separated from the first longitudinal center line by about 100 to about 140 degrees about the longitudinal axis of the tubular body.

14. The sleeve according to claim 13, wherein first pocket is radially separated from the second pocket by an intermediate arc having an angle from 10 degrees to 55 degrees.

15. The sleeve according to claim 13, wherein the first pocket and second pocket each comprise a front side facing an outside of the tubular body and a back side facing the hollow center, and wherein the front side is partially open and the backside is closed and defines a portion of the hollow center of the sleeve.

16. The sleeve according to claim 13, further comprising an orientation protrusion extending axially from one of the first and second open ends.

17. The sleeve according to claim 13, wherein the sleeve is sized to fit over a body of the medical lead.

18. The sleeve according to claim 13, wherein the first inactive imaging marker and the second inactive imaging marker are radio opaque.

* * * * *